(12) United States Patent
Valarche et al.

(10) Patent No.: US 8,962,311 B2
(45) Date of Patent: Feb. 24, 2015

(54) METHOD OF OBTAINING CHICKEN EMBRYONIC STEM CELLS

(75) Inventors: Isabelle Valarche, Nantes (FR); Luc Batard, Nantes (FR); Majid Mehtali, Coueron (FR); Fabienne Guehenneux, Le Temple de Bretagne (FR)

(73) Assignee: Valneva, Lyons (FR)

( * ) Notice: Subject to any disclaimer, the term of this patent is extended or adjusted under 35 U.S.C. 154(b) by 955 days.

(21) Appl. No.: 12/376,660

(22) PCT Filed: Aug. 9, 2007

(86) PCT No.: PCT/EP2007/058263
§ 371 (c)(1),
(2), (4) Date: Apr. 21, 2010

(87) PCT Pub. No.: WO2008/017704
PCT Pub. Date: Feb. 14, 2008

(65) Prior Publication Data
US 2010/0235937 A1    Sep. 16, 2010

Related U.S. Application Data

(60) Provisional application No. 60/836,378, filed on Aug. 9, 2006.

(51) Int. Cl.
*C12N 5/00* (2006.01)
*A01K 67/027* (2006.01)

(52) U.S. Cl.
USPC ........................................... 435/325; 800/19

(58) Field of Classification Search
USPC .................... 800/19; 435/455, 325
See application file for complete search history.

(56) References Cited

U.S. PATENT DOCUMENTS

| | | | |
|---|---|---|---|
| 5,162,215 | A | 11/1992 | Bosselman et al. |
| 5,340,740 | A | 8/1994 | Petitte et al. |
| 5,453,357 | A | 9/1995 | Hogan |
| 5,589,458 | A | 12/1996 | Jameson et al. |
| 5,656,479 | A | 8/1997 | Petitte et al. |
| 5,830,510 | A | 11/1998 | Petitte et al. |
| 6,114,168 | A | 9/2000 | Samarut et al. |
| 6,500,668 | B2 | 12/2002 | Samarut et al. |
| 6,656,479 | B2 | 12/2003 | Brake et al. |
| 6,998,266 | B2 | 2/2006 | Samarut et al. |
| 7,432,101 | B2 | 10/2008 | Guehenneux et al. |
| 7,771,980 | B2 | 8/2010 | Guehenneux et al. |
| 8,148,132 | B2 | 4/2012 | Mehtali et al. |
| 2002/0192815 | A1 | 12/2002 | Samarut et al. |
| 2004/0058441 | A1 | 3/2004 | Pain |
| 2004/0077086 | A1 | 4/2004 | Reiter et al. |
| 2009/0239297 | A1 | 9/2009 | Pain et al. |
| 2010/0062489 | A1 | 3/2010 | Guehenneux et al. |
| 2010/0111999 | A1 | 5/2010 | Guehenneux et al. |
| 2010/0221825 | A1 | 9/2010 | Pain et al. |
| 2011/0294209 | A1 | 12/2011 | Pain et al. |
| 2012/0238001 | A1 | 9/2012 | Mehtali et al. |
| 2014/0154741 | A1 | 6/2014 | Guehenneux et al. |

FOREIGN PATENT DOCUMENTS

| | | |
|---|---|---|
| CN | 1826406 | 8/2006 |
| EP | 1 149 899 A1 | 10/2001 |
| EP | 0 787 180 B1 | 9/2002 |
| JP | 5-227947 A | 9/1993 |
| WO | WO 90/01541 A1 | 2/1990 |
| WO | WO 93/15185 A1 | 8/1993 |
| WO | WO 93/23528 A1 | 11/1993 |
| WO | WO 94/03585 A1 | 2/1994 |
| WO | WO 96/12793 A1 | 5/1996 |
| WO | WO 98/15614 A1 | 4/1998 |
| WO | WO 99/06533 A1 | 2/1999 |
| WO | WO 99/06534 A1 | 2/1999 |
| WO | WO 00/03000 A2 | 1/2000 |
| WO | WO 00/47717 A1 | 8/2000 |
| WO | WO 01/26294 A1 | 4/2001 |
| WO | WO 03/076601 A1 | 9/2003 |
| WO | WO 2005/007840 A1 | 1/2005 |
| WO | WO 2006/108846 A1 | 10/2006 |
| WO | WO 2007/135133 A1 | 11/2007 |
| WO | WO 2008/129058 A1 | 10/2008 |

OTHER PUBLICATIONS

Bird Classification/Families of the Eastern US Birds, 2009.*
Pain (1996, Development, vol. 122, p. 2339-2348).*
Trentin (PNAS, Mar. 30, 2004, vol. 101, No. 13, p. 4495-4500).*
Bosselman et al., "*Transmission of exogenous genes into the chicken,*" 41 Journal of Reproduction and Fertility Supplement 183-195 (1990).
Carsience et al., "*Germline chimeric chickens from dispersed donor blastodermal cells and compromised recipient embryos,*" 117 Development 669-675 (1993).
Chang et al., "*Proliferation of Chicken Primordial Germ Cells Cultured on Stroma Cells From the Germinal Ridge,*" 19(2) Cell Biology International 143-149 (1995).

(Continued)

*Primary Examiner* — Michael C. Wilson
(74) *Attorney, Agent, or Firm* — Wolf, Greenfield & Sacks, P.C.

(57) ABSTRACT

Method of culturing embryonic stem (ES) cells of avian origin includes the steps of: a) suspending ES cells originating from the blastoderm disk of fertilized un-incubated avian egg(s) in a basal culture medium supplemented with: insulin-like growth factor-1 (IGF-1) and ciliary neurotrophic factor (CNTF); and animal serum; and, optionally, at least one growth factor selected from among interleukin 6 (Il-6), interleukin 6 receptor (Il-6R), stem cell factor (SCF), fibroblast growth factor (FGF), leukemia inhibitory factor (LIF), interleukin 11 (Il-11), oncostatin and/or cardiotrophin; b) seeding the suspension of ES cells obtained in step a) on a layer of feeder cells and further culturing the ES cells for at least 2 to 10 passages; c) optionally, removing at least one growth factor selected from among SCF, FGF, Il-6, Il-6R, LIF, oncostatin, cardiotrophin and Il-11 from the culture medium; and d) further culturing the ES cells in the medium of step c) on a layer of feeder cells.

11 Claims, 9 Drawing Sheets

(56) References Cited

OTHER PUBLICATIONS

Figure 1:
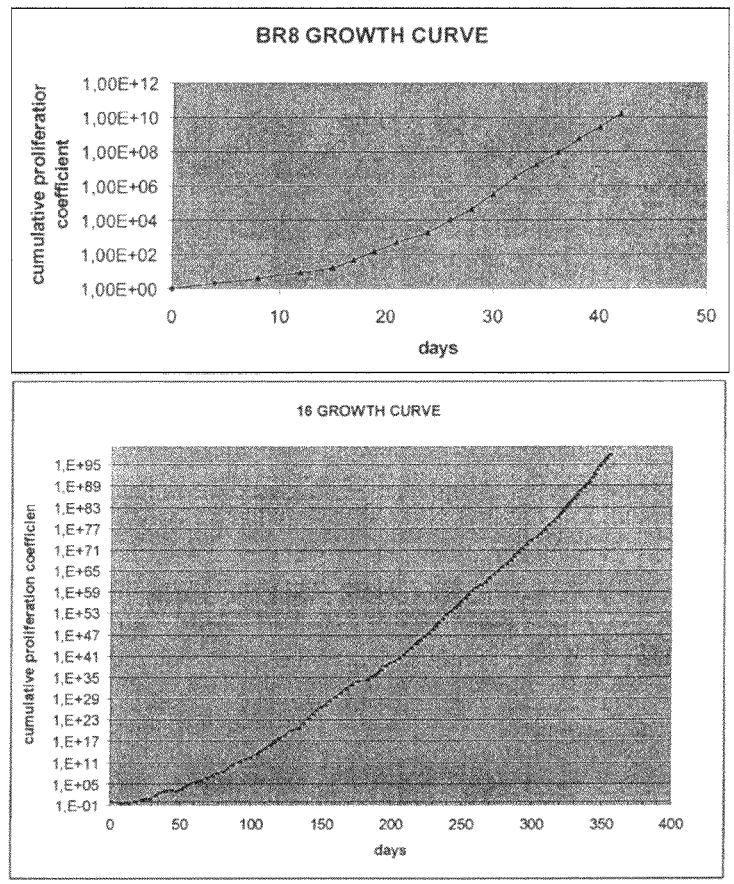

Chang et al., "*Simple Method for Isolation of Primordial Germ Cells From Chick Embryos,*" 16(9) Cell Biology International Reports 853-857 (1992).

Etches et al., "*Contributions to Somatic and Germline Lineages of Chicken Blastodermal Cells Maintained in Culture,*"45 Molecular Reproduction and Development 291-298 (1996).

Eyal-Giladi et al., "*From Cleavage to Primitive Streak Formation: A Complementary Normal Table and a New Look at the First Stages of the Development of the Chick,*" 49 Developmental Biology 321-337 (1976).

Forster et al., "*Tetracycline-inducible expression systems with reduced basal activity in mammalian cells,*" 27(2) Nucleic Acids Research 708-710 (1999).

Gerner et al., "*Heat-inducible vectors for use in gene therapy,*" 16(2) International Journal of Hyperthermia 171-181 (2000).

Ginsburg et al., "*Primordial germ cells of the young chick blastoderm originate from the central zone of the area pellucida irrespective of the embryo-forming process,*" 101 Development 209-219 (1987).

Hagihara et al., "*Long-Term Assessment of Encapsulated Cells Transfected With Tet-On System,*" 8 Cell Transplantation 431-434 (1999).

Hahnel et al., "*The distribution of two cell surface determinants of mouse embryonal carcinoma and early embryonic cells,*" 10 Journal of Reproductive Immunology 89-110 (1987).

Halloran et al., "*Laser-induced gene expression in specific cells of transgenic zebra fish,*" 127 Development 1953-1960 (2000).

Hamburger et al., "*A Series of Normal Stages in the Development of the Chick Embryo,*" 88(1) Journal of Morphology 231-272 (1992).

Huang et al., "*Expression of Green Fluorescent Protein in Oligodendrocytes in a Time- and Level-Controllable Fashion with a Tetracycline-Regulated System,*" 5 Molecular Medicine 129-137 (1999).

Karagenc et al., "*Origin of Primordial Germ Cells in the Prestreak Chick Embryo,*" 19 Developmental Genetics 290-301 (1996).

Kawase et al., "*Strain difference in establishment of mouse embryonic stem (ES) cell lines,*" 38 International Journal of Developmental Biology 385-390 (1994).

Kemler et al., "*Reactivity of monoclonal antibodies against intermediate filament proteins during embryonic development,*" 64 Journal of Embryology & Experimental Morphology 45-60 (1981).

Liu et al., "*LAC/TET Dual-Inducible System Functions in Mammalian Cell Lines,*" 24(4) BioTechniques 624-632 (Apr. 1998).

Love et al., "*Transgenic Birds by DNA Microinjection,*" 12 Bio/Technology 60-63 (Jan. 1994).

Naito et al., "*Production of Germline Chimeric Chickens, With high Transmission Rate of Donor-Derived Gametes, Produced by Transfer of Primordial Germ Cells,*" 39 Molecular Reproduction and Development 153-161 (1994).

Nieuwkoop et al., "*Chapter 7: The migration of the primordial germ cells,*" Primordial Germ Cells in the Chordates: Embryogenesis and Phylogenesis (1979).

Petitte et al., "*Production of somatic and germline chimeras in the chicken by transfer of early blastodermal cells,*" 108 Development 185-189 (1990).

Petitte et al., "*The Origin of the Avian Germ Line and Transgenesis in Birds,*" 76 Poultry Science 1084-1092 (1997).

Rang et al., "*The tetracycline-responsive promoter contains functional interferon-inducible response elements,*" 28(5) Nucleic Acids Research 1120-1125 (2000).

Sellier et al., "*Comparative Staging of Embryo Development in Chicken, Turkey, Duck, Goose, Guinea Fowl, and Japanese Quail Assessed from Five Hours After Fertilization Through Seventy-Two Hours of Incubation,*" 15 Journal of Applied Poultry Research 219-228 (2006).

Smith et al., "*Buffalo Rat Liver Cells Produce a Diffusible Activity Which Inhibits the Differentiation of Murine Embryonal Carcinoma and Embryonic Stem Cells,*" 121 Developmental Biology 1-9 (1987).

Solter et al., "*Monoclonal antibody defining a stage-specific mouse embryonic antigen (SSEA-1),*" 75(11) Proceedings of the National Academy of Sciences USA 5565-5569 (Nov. 1978).

Thoraval et al., "*Somatic and Germline Chicken Chimeras Obtained from Brown and White Leghorns by Transfer of Early Blastodermal Cells,*" 73 Poultry Science 1897-1905 (1994).

Tsunekawa et al., "*Isolation of chicken vasa homolog gen and tracing the origin of primordial germ cells,*" 127 Development 2741-2750 (2000).

Uchida et al., "*Rapid and Sustained Hematopoietic Recovery in Lethally Irradiated Mice Transplanted With Purified Thy-1.1$^{10}$ Lin$^-$ Sca-1$^+$ Hematopoietic Stem Cells,*" 83(12) Blood 3758-3779 (Jun. 15, 1994).

Wilkinson et al., "*Expression pattern of the mouse T gene and its role in mesoderm formation,*" 343 Nature 657-659 (Feb. 15, 1990).

Yasuda et al., "*A method to obtain avian germ-line chimaeras using isolated primordial germ cells,*" 96 Journal of Reproductive Fertility 521-528 (1992).

Zhu et al., "*Production of human monoclonal antibody in eggs of chimeric chickens,*" 23 Nature Biotechnology 1-11 (Aug. 28, 2005).

van de Lavoir et al., "Germline transmission of genetically modified primordial germ cells", Nature, 2006, pp. 766-769, vol. 441, No. 7094, London.

Pain et al., "Long-term in vitro culture and characterisation of avian embryonic stem cells with multiple morphogenetic potentialities", Development, 1996, pp. 2339-2348—vol. 122, Great Britain.

Petitte et al., "Avian pluripotent stem cells", Mechanisms of Development, 2004, pp. 1159-1168, vol. 121, Ireland.

Thoraval et al., "Germline transmission of exogenous genes in chickens using helper-free ecotropic avian leukosis virus-based vectors", Transgenic Research, 1995, pp. 369-376, vol. 4.

van de Lavoir et al., "High-grade transgenic somatic chimeras from chicken embryonic stem cells", Mechanisms of Development, 2006, pp. 31-41, vol. 123.

Wang et al., "Progress Towards the Culture and Transformation of Chicken Blastodermal Cells", Stem Cells, 2006, pp. 1638-1645, vol. 24, No. 7.

Acloque et al., Identification of a new gene family specifically expressed in chicken embryonic stem cells and early embryo. Mech Dev. May 2001;103(1-2):79-91.

Chang et al., Germ line chimera produced by transfer of cultured chick primordial germ cells. Cell Biol Int. Jul. 1995;19(7):569-76.

Chang et al., Production of germline chimeric chickens by transfer of cultured primordial germ cells. Cell Biol Int. Aug. 1997;21(8):495-9.

Chino et al., Skin reaction to yellow fever vaccine after immunization with rabies vaccine of chick embryo cell culture origin. Jpn J Infect Dis. Apr. 1999;52(2):42-4.

Crocker et al., Isolation and characterization of resident stromal macrophages and hematopoietic cell clusters from mouse bone marrow. J Exp Med. Sep. 1, 1985;162(3):993-1014.

De Paulsen et al., Role of transforming growth factor-alpha in von Hippel-Lindau (VHL)$^{-/-}$ clear cell renal carcinoma cell proliferation: a possible mechanism coupling VHL tumor suppressor inactivation and tumorigenesis. Proc Natl Acad Sci U S A. Feb. 13, 2001;98(4):1387-92. Epub Feb. 6, 2001.

Drexler et al., Highly attenuated modified vaccinia virus Ankara replicates in baby hamster kidney cells, a potential host for virus propagation, but not in various human transformed and primary cells. J Gen Virol. Feb. 1998;79 ( Pt 2):347-52.

Dunwiddie et al., Presence of retrovirus reverse transcriptase-related gene sequences in avian cells lacking endogenous avian leukosis viruses. Proc Natl Acad Sci U S A. Aug. 1985;82(15):5097-101.

Enami et al., High-efficiency formation of influenza virus transfectants. J Virol. May 1991;65(5):2711-3.

Enami et al., Introduction of site-specific mutations into the genome of influenza virus. Proc Natl Acad Sci U S A. May 1990;87(10):3802-5.

Etches et al., Manipulation of blastodermal cells. Poult Sci. Aug. 1997;76(8):1075-83.

Ettenberg et al., cbl-b inhibits epidermal growth factor receptor signaling. Oncogene. Mar. 11, 1999;18(10):1855-66.

(56) References Cited

OTHER PUBLICATIONS

Fayette et al., Human dendritic cells skew isotype switching of CD40-activated naive B cells towards IgA1 and IgA2. J Exp Med. Jun. 2, 1997;185(11):1909-18.

Ferlin-Bezombes et al., IFN-alpha is a survival factor for human myeloma cells and reduces dexamethasone-induced apoptosis. J Immunol. Sep. 15, 1998;161(6):2692-9.

Gardner et al., Reflections on the biology of embryonic stem (ES) cells. Int J Dev Biol. Apr. 1997;41(2):235-43.

Gey et al., Long-term growth of chicken fibroblasts on a collagen substrate. Exp Cell Res. Mar. 15, 1974;84(1):63-71.

Horiuchi et al., Chicken leukemia inhibitory factor maintains chicken embryonic stem cells in the undifferentiated state. J Biol Chem. Jun. 4, 2004;279(23):24514-20. Epub Mar. 25, 2004.

Hussain et al., Identification and characterization of avian retroviruses in chicken embryo-derived yellow fever vaccines: investigation of transmission to vaccine recipients. J Virol. Jan. 2003;77(2):1105-11.

Johnson et al., Characterization of endogenous avian leukosis viruses in chicken embryonic fibroblast substrates used in production of measles and mumps vaccines. J Virol. Apr. 2001;75(8):3605-12.

Kaaden et al., Establishment and characterization of chicken embryo fibroblast clone LSCC-H32. In Vitro. Oct. 1982;18(10):827-34.

Karagenç et al., Soluble factors and the emergence of chick primordial germ cells in vitro. Poult Sci. Jan. 2000;79(1):80-5.

Kemble et al., Novel generations of influenza vaccines. Vaccine. May 1, 2003;21(16):1789-95.

Kempe, Smallpox vaccination of eczema patients with attenuated live vaccinia virus. Yale J Biol Med. Aug. 1968;41(1):1-12.

Kingsley et al., Infectious laryngotracheitis virus, an alpha herpesvirus that does not interact with cell surface heparan sulfate. Virology. Apr. 10, 1999;256(2):213-9.

Kyhse-Andersen, Electroblotting of multiple gels: a simple apparatus without buffer tank for rapid transfer of proteins from polyacrylamide to nitrocellulose. J Biochem Biophys Methods. Dec. 1984;10(3-4):203-9.

Laemmli, Cleavage of structural proteins during the assembly of the head of bacteriophage T4. Nature. Aug. 15, 1970;227(5259):680-5.

Linial, A line of ring-necked pheasant cells susceptible to infection by avian oncornaviruses. Virology. Sep. 1976;73(2):548-52.

Lovatt et al., High throughput detection of retrovirus-associated reverse transcriptase using an improved fluorescent product enhanced reverse transcriptase assay and its comparison to conventional detection methods. J. Virol. Methods. 1999;82:185-200.

Luytjes et al., Amplification, expression, and packaging of foreign gene by influenza virus. Cell. Dec. 22, 1989;59(6):1107-13.

Maruyama et al., The antigenicity of chicken embryo fibrosis cell passaged strains of Japanese encephalitis viruses. Journal of Infection and Chemotherapy, vol. 60, pp. 251-256 (1986).

Matsui et al., Derivation of pluripotential embryonic stem cells from murine primordial germ cells in culture. Cell. Sep. 4, 1992;70(5):841-7.

Mullins et al., Transgenesis in the rat and larger mammals. J Clin Invest. Apr. 1, 1996;97(7):1557-60.

Nazerian, An updated list of avian cell lines and transplantable tumours. Avian Pathol. 1987;16(3):527-44.

Ogura et al., Establishment of two chick embryo fibroblastic cell lines. Gann. May 1984;75(5):410-4.

Piquet-Pellorce et al., Are LIF and related cytokines functionally equivalent? Exp Cell Res. Aug. 1994;213(2):340-7.

Reed et al., A simple method of estimating fifty percent endpoints. Am. J. Hyg. 1938; 27:493-497.

Resnick et al., Phylogenetic distribution of the novel avian endogenous provirus family EAV-0. J Virol. Oct. 1990;64(10):4640-53.

Shafren et al., Pathogenesis of avian encephalomyelitis viruses. J Gen Virol. Nov. 1991;72 (Pt 11):2713-9.

Sugimoto et al., Characteristics of an attenuated vaccinia virus strain, LC16m0, and its recombinant virus vaccines. Vaccine. Jun. 1994;12(8):675-81.

Tartaglia et al., NYVAC: a highly attenuated strain of vaccinia virus. Virology. May 1992;188(1):217-32.

Tsang et al., Evidence of avian leukosis virus subgroup E and endogenous avian virus in measles and mumps vaccines derived from chicken cells: investigation of transmission to vaccine recipients. J Virol. Jul. 1999;73(7):5843-51.

Weissmahr et al., Reverse transcriptase activity in chicken embryo fibroblast culture supernatants is associated with particles containing endogenous avian retrovirus EAV-0 RNA. J Virol. Apr. 1997;71(4):3005-12.

Wood et al., An improved single-radial-immunodiffusion technique for the assay of influenza haemagglutinin antigen: application for potency determinations of inactivated whole virus and subunit vaccines. J Biol Stand. 1977;5(3):237-47.

Yang et al., Use of avian cytokines in mammalian embryonic stem cell culture. Poult Sci. Jul. 1994;73(7):965-74.

\* cited by examiner

METHOD OF OBTAINING CHICKEN EMBRYONIC STEM CELLS

CROSS-REFERENCE TO PRIORITY/PCT APPLICATIONS

This application claims priority under 35 U.S.C. §119 of U.S. Provisional Application No. 60/836,378, filed Aug. 9, 2006, and is a continuation/national phase of PCT/EP 2007/058263, filed Aug. 9, 2007 and designating the United States (published in the English language on Feb. 14, 2008, as WO 2008/017704 A1; the title and abstract were also published in English), each hereby expressly incorporated by reference in its entirety and each assigned to the assignee hereof.

The present invention relates to avian biotechnology and in particular to a method of producing transgenic birds. The invention is particularly useful to generate transgenic birds expressing high amount of a recombinant protein of interest in egg.

With over 400 biomolecules in clinical development and a market of over 30 billions dollars, the therapeutic field has witnessed an accelerated growth in the last fifteen years. Most recombinant proteins require specific post-translational modifications for full biological activities and must thus be produced in mammalian cells grown in large-scale bio-reactors. The cost associated with such production system, combined with important quantitative needs is responsible for increasing delays in the overall process of product development. In this context, transgenic animals could represent an economically attractive alternative, especially if the modification could be transmitted to the progeny through the germ-line.

While rabbits, goats and cows have elicited plenty of interest, the hen has long been considered as the most appealing biological production system for fast and cost-effective production of recombinant therapeutic proteins in chicken eggs. The chicken egg-laying capabilities are indeed remarkable since commercial hen lays about 250 eggs a year, each egg containing nearly 4 grams of egg white proteins. If only 100 mg of recombinant proteins were to be produced in an egg, a small flock of 1000 hens would thus be able to produce 25 kg of raw recombinant proteins material a year. In addition, the commercial egg industry is already highly automated and regulatory agencies are comfortable with egg-derived products since many human vaccines are produced in the chicken eggs since decades.

Likewise, the poultry industry may also have interest in using transgenesis for accelerated selection of genetic traits of commercial interest (i.e "meta-cloning technology"). The idea would be to bypass the classical selection scheme: [Pedigree→GGP→GP→PS] to get in a shorter time the desired chick. The most likely use of transgenic technology in poultry production could be to impart disease resistance which is a common practise in transgenic plants or to improve food assimilation. In addition, transgenic technology could be a strategy to conserve avian genetic resources. So far, the splitting into different places of pedigree animals, the most valuable animals in poultry industry, is the only way to prevent the loss of years of selection programs in case of troubles (eg. viral infections) in a breeding facility. Such an approach is expensive and does not guarantee against national sanitary decisions enforcing the preventive elimination of all local poultry to check viral infection, as in the Netherlands in 2003.

The engineering of a modified animal implies first the stable introduction of the transgene into the genome of the animal. The different technologies to introduce DNA investigated since 25 years are: (i) the DNA micro-injection, (ii) the viral transduction, (iii) the sperm-mediated gene transfer, (iv) the nuclear transfer, the cell-based transfer using (v) primordial germ cells, or (vi) embryonic stem cells. In the chick, only the DNA micro-injection approach (Love et al, 1994 Biotechnology 12:60-63) and the viral transduction (Bosselman et al, 1990 J. Reprod. Fertil. Suppl. 41: 183-195) have been validated for germ line transmission of the transgene. However, these two technologies suffer from several limitations; they are cumbersome and laborious and have a low efficacy, partly due to random integration and silencing of the transgene. Viral transduction technology has the additional limitation of the transgene size to be incorporated into the viral vector. These two technologies did not allow today to reach protein expression level compatible with commercial developments.

Injection into the developing chick embryo of primordial germ cells (PGC) or Embryonic Stem (ES) cells, previously in vitro genetically engineered are among the promising technologies of avian transgenesis especially because these technologies allow targeting transgene integration to specific sites within the genome which should allow high expression levels of the transgene. However, in order to use this approach to produce transgenic chicks, an important prerequisite must be fulfilled: cells must survive to in vitro manipulations, while still maintaining their ability to be incorporated within a recipient embryo, to colonize the germ-line and then to transmit the modification to the progeny.

In the past, many attempts were made to overcome the different technical hurdles at each process steps and today, somatic and germ-line chimera had been obtained by injection of freshly isolated blastodermal cells isolated from unincubated embryos into the sub-germinal cavity of freshly laid embryos. Donor and recipient cells contribution was assessed in (i) the melanocyte population through examination of black and white pigmentation (Barred Rocks or Brown Leghorns have a recessive allele at the I locus while the White Leghorns have a dominant allele at the I locus); (ii) the erythrocyte population through analysis of DNA fingerprints; (iii) the gonads through the analysis of the progeny with a donor-derived phenotype (Petitte et al, 1990 Development 108:185-189; Carsience et al, 1993 Development 117:669-675; Thoraval et al, 1994 Poultry Science 73:1897-1905; Pain et al, 1996 Development 122:2339-2348). Chimera with contributions to both somatic tissues and the germline were observed when blastodermal cells were injected after 48 hours (Etches et al, 1996 Mol. Reprod. Dev. 45:291-288) up to 7 days of culture (Pain et al, 1996). Etches et al, 1996, had demonstrated that significantly more somatic chimeras were observed following the injection of cells co-cultured with mouse fibroblasts. Pain et al (1996) seeded avian blastodermal cells on STO mouse fibroblast cell line. The ES status of cells maintained in culture relied on the expression of the ECMA-7 and SSEA-1 epitopes and the telomerase activity (Pain et al, 1996). Proliferation in the absence of differentiation of blastodermal cells was stimulated by the presence of Leukemia Inhibitory Factor (LIF) and other factors, Il-11, SCF, bFGF, IGF-1 and differentiation was inhibited by exposure to anti-retinoic acid monoclonal antibody (Pain et al, 1996). It had been shown that colonization of the embryo by donor-derived cells was facilitated when the recipient embryo was compromised by exposure to irradiation prior to injection of the donor cells (Carsience et al, 1993).

However, blastodermal cells maintained in culture yielded fewer chimeras that exhibit reduced contributions to somatic tissues in comparison to the frequency and extent of somatic chimerism observed following injection of freshly prepared cells. Moreover, even so it was demonstrated that each of the component parts of the cell-based avian transgenesis strategy could be accomplished; no transgenic animal had been described that were obtained with the ES cell technology.

It remains a need for efficient methods of generating transgenic chickens. This is the object of the instant invention.

To achieve this object and in accordance with the purpose of the invention, as embodied and broadly described herein, the present invention provides a method of culturing embryonic stem (ES) cells of avian, comprising the steps of:
a) suspending ES cells originating from the blastoderm disk of fertilized, preferably un-incubated, avian egg(s) in a basal culture medium supplemented with:
  insulin-like growth factor-1 (IGF-1) and/or ciliary neurotrophic factor (CNTF); and
  optionally, at least one growth factors selected in the group comprising interleukin 6 (Il-6), interleukin 6 receptor (Il-6R), stem cell factor (SCF), fibroblast growth factor (FGF), leukaemia inhibitory factor (LIF), interleukin 11 (Il-11), oncostatin and cardiotrophin; and
  animal serum;
b) seeding the suspension of ES cells obtained in step a) on a layer of feeder cells and further culturing the ES cells for at least between 2 to 10 passages, preferably between 2 to 20 passages;
c) optionally removing at least one growth factors selected SCF, FGF, Il-6, Il-6R, LIF, oncostatin, cardiotrophin and Il-11 from the culture medium;
d) further culturing the ES cells in the medium of step c) on a layer of feeder cells.

In a preferred embodiment, the method of culturing embryonic stem (ES) cells of avian of the invention, comprises the steps of:
a) suspending ES cells originating from the blastoderm disk of fertilized, preferably, un-incubated avian egg(s) in a basal culture medium supplemented with insulin-like growth factor-1 (IGF-1), ciliary neurotrophic factor (CNTF), interleukin 6 (Il-6), interleukin 6 receptor (Il-6R), stem cell factor (SCF) and fibroblast growth factor (FGF) and animal serum;
b) seeding the suspension of ES cells obtained in step a) on a layer of feeder cells and further culturing the ES cells for at least between 2 to 10 passages, preferably between 2 to 20 passages;
c) optionally removing at least one growth factor selected from the group comprising SCF, FGF, Il-6 and Il-6R from the culture medium, and preferably removing the growth factors SCF, FGF, IL-6 and IL-6R from the culture medium;
d) further culturing the ES cells in the medium of step c) on a layer of feeder cells.

In another preferred embodiment, the method of culturing embryonic stem (ES) cells of avian of the invention, comprises the steps of:
a) suspending ES cells originating from the blastoderm disk of fertilized, preferably un-incubated avian egg(s) in a basal culture medium supplemented with insulin-like growth factor-1 (IGF-1), ciliary neurotrophic factor (CNTF), interleukin 6 (Il-6), interleukin 6 receptor (Il-6R), stem cell factor (SCF), fibroblast growth factor (FGF) and animal serum;
b) seeding the suspension of ES cells obtained in step a) on a layer of feeder cells and further culturing the ES cells for at least between 2 to 10 passages;
c) optionally removing at least one growth factor selected from the group comprising SCF and FGF from the culture medium; and preferably removing both growth factors SCF and FGF from the culture medium;
d) further culturing the ES cells in the medium of step c) on a layer of feeder cells.

The optional step c) of the method of the invention is performed when signs of mortality and/or differentiation of ES cells are observed into culture. Examples of sign of differentiation are for example morphological changes of cells to a characteristic morphological type, such as for example epithelial cell type or fibroblast cell type. Another example of differentiation may be the absence or the decrease of expression of ES cells markers, such as telomerase, alkaline phosphatase, SSEA-1 antigen which are ES cells markers.

In a more preferred embodiment, the method of culturing embryonic stem (ES) cells of avian, of the invention comprises the steps of:
a) suspending ES cells originating from the blastoderm disk of fertilized, preferably un-incubated, avian egg(s) in a basal culture medium supplemented with at least insulin-like growth factor-1 (IGF-1), ciliary neurotrophic factor (CNTF), interleukin 6 (Il-6), interleukin 6 receptor (Il-6R), stem cell factor (SCF), fibroblast growth factor (FGF) and animal serum;
b) seeding the suspension of ES cells obtained in step a) on a layer of feeder cells and further culturing the ES cells in the medium of step a).

In another more preferred embodiment, the method of culturing embryonic stem (ES) cells of avian, of the invention comprises the steps of:
a) suspending ES cells originating from the blastoderm disk of fertilized un-incubated avian egg(s) in a basal culture medium supplemented with at least insulin-like growth factor-1 (IGF-1), ciliary neurotrophic factor (CNTF), interleukin 6 (Il-6), interleukin 6 receptor (Il-6R) and animal serum;
b) seeding the suspension of ES cells obtained in step a) on a layer of feeder cells and further culturing the ES cells in the medium of step a).

In another more preferred embodiment, the method of culturing embryonic stem (ES) cells of avian, of the invention comprises the steps of:
a) suspending ES cells originating from the blastoderm disk of fertilized un-incubated avian egg(s) in a basal culture medium supplemented with at least insulin-like growth factor-1 (IGF-1), ciliary neurotrophic factor (CNTF) and animal serum;
b) seeding the suspension of ES cells obtained in step a) on a layer of feeder cells and further culturing the ES cells in the medium of step a).

The term <<avian>> as used herein is intended to refer to any species, subspecies or race of organism of the taxonomic class <<ava>>, such as, but not limited to, chicken, turkey, duck, goose, quails, pheasants, parrots, finches, hawks, crows, ostrich, emu and cassowary. The term "avian, "bird", "ayes" or "ava" as used herein is intended to have the same meaning, and will be used indistinctly. In a preferred embodiment, "birds" refer to any animal of the taxonomix order:
  "Anseriformes" (i.e duck, goose, swan and allies). The order Anseriformes contains about 150 species of birds in three families: the Anhimidae (the screamers), Anseranatidae (the Magpie-goose), and the Anatidae, which includes over 140 species of waterfowl, among them the ducks, geese, and swans. All species in the order are highly adapted for an aquatic existence at the water surface. All are web-footed for efficient swimming (although some have subsequently become mainly terrestrial). The term includes the various strains of ducks, for example Pekin duck and Muscovy duck.

"Galliformes" (i.e chicken, quails, turkey, pheasant and allies). The Galliformes is an order of birds containing the chicken, turkeys, quails and pheasants. About 256 species are found worldwide. The term includes the various strains of *Gallus gallus*, or chickens, for example S86N, Valo, White Leghorn, Brown Leghorn, Sussex, New Hampshire, Rhode Island, Ausstralorp, Minorca, Amrox, California Gray, East Lansing, Italian-Partridge-colored, Marans, Barred Rock, Cou Nu Rouge (CNR), GF30, ISA as well as strains of turkeys, pheasants, quails, and other poultry commonly bred.

"Columbiformes" (i.e Pigeon and allies). The bird order Columbiformes includes the very widespread doves and pigeons.

In a preferred embodiment, the avian cell of the present invention is a chicken cell. The chicken is preferably selected from the group of chicken strains comprising S86N, Valo, White Leghorn, Brown Leghorn, Sussex, New Hampshire, Rhode Island, Ausstralorp, Minorca, Amrox, California Gray, East Lansing, Italian-Partridge-colored, Marans, Barred Rock, Cou Nu Rouge (CNR), GF30, ISA, In a more preferred embodiment, the chicken ES cell of the present invention is a Barred-Rock strain. In another preferred embodiment, the avian cell of the present invention is a duck cell. In a more preferred embodiment, the duck ES cell of the present invention is a Pekin or Muscovy strain.

The cells of step a) are avian embryonic stem cells. Embryonic stem cells (ES cells) are stem cells which have the characteristic feature of being obtained from culturing parts or all of a very early embryo (e.g blastula stage). These ES cells exhibit in vitro all the characteristics of a stem cell, and in vivo the unique capacity of contributing to the morphogenesis of an embryo and of participating in germline colonization when they are re-implanted in any manner whatsoever in a recipient embryo. Primordial Germ Cells (PGC) which are the progenitors of the sperm or ovocyte cells that develop after sexual maturity are pluripotent ES cells and constitutes a subtype of ES cells. Preferably, avian embryonic stem cells of the invention are isolated from the blastoderm disk of fertilized avian egg(s) at development stage comprises between stages VI and XII of Eyal-Giladi & Kochav's classification, and more preferably around the stage X of Eyal-Giladi & Kochav's classification (see EYAL-GILADI's classification: EYAL-GILADI and KOCHAV, 1976, <<*From cleavage to primitive streak formation: a complementary normal table* and *a new look at the first stages of the development in the chick*>>. "General Morphology" Dev. Biol. 49: 321-337). In a preferred embodiment, the cells of step a) are isolated from freshly laid fertilized eggs that is to say at a developmental stage named oviposition. According to Sellier et al. (2006, J. Appl. Poult. Res., 15:219-228), oviposition corresponds to the following development stages according to Eyal-Giladi's classification:

Muscovy duck: stage VII
Guinea fowl: stage VII-VIII
Turkey: stage VII-VIII
Pekin duck: stage VIII
Chicken: Stage X
Japanese Quail: stage XI
Goose: stage XI.

Preferably, the Pekin duck embryonic stem (ES) cells of step a) is obtained by dissociating embryo(s) at around stage VIII (oviposition) of Eyal-Giladi's classification.

Preferably, the Muscovy duck embryonic stem (ES) cells of step a) is obtained by dissociating embryo(s) at around stage VII (oviposition) of Eyal-Giladi's classification.

Preferably, the chicken embryonic stem (ES) cells of step a) is obtained by dissociating embryo(s) at around stage X (oviposition) of Eyal-Giladi's classification.

More preferably, the eggs have never been incubated (i.e "un-incubated"). The cells isolated from blastoderm disk comprises avian embryonic cells, more particularly avian embryonic stem (ES) cells; these avian embryonic cells are totipotent or pluripotent cells. Blastoderma cells are tightly connected cells that grow as colonies; they display a round-shaped morphology, with a big nucleus and a small cytoplasm (see FIG. 2). The morphology of the blastodermal cells evolves during the culture (steps FIGS. 2 *b & c* of the method of the invention) from tightly connected cells to more dispersed cells with looser connections. Avian ES cells obtained at step c) preferably display looser connections.

According to another embodiment, the cells of step a) are a population of embryonic stem cells enriched in primordial germ cells (PGC). More preferably, the avian ES cells of step a) are purified PGCs. In avian species, Primordial Germ Cells arise from the central region of the blastoderm (Ginsburg and Eyal-Giladi, 1987 Development 101(2):209-19; Karagenc et al, 1996 Dev Genet. 19(4):290-301; Petitte et al, 1997 Poult Sci. 76(8):1084-92). Then they move to an anterior, extra-embryonic site, the germinal crescent until collected by the vasculature between 2.5 and 5 days of embryonic development to reach the germinal ridge. They colonize the germinal ridge where they eventually differentiate into oocytes or spermatocytes (Nieuwkoop and Sutasurya, 1979. *The Migration of the primordial germ cells. In: Primordial germ cell in Chordates*. London: Cambridge University Press p 113-127). Methods for isolation of PGCs from donor avian embryos have been reported in the literature and can easily be performed by one skilled in the art (See, e.g. JP924997 published Sep. 7, 1993 Pub. N° 05-227947; Chang et al. 1992. Cell Biol. Int. 19(2): 143-149; Naito et al. 1994 Mol. Reprod. Dev. 39: 153-161; Yasuda et al. 1992. J. Reprod. Fert. 96: 521-528; Chang et al. 1992 Cell Biol. Int. Reporter 16(9): 853-857). According to an embodiment. PGCs are collected from embryonic blood collected from the dorsal aorta of a chicken embryo at stage 12-14 of Hamburger & Hamilton's classification (Hamburger & Hamilton 1951 A series of normal stages in the development of chick embryo. J. Morphol. 88: 49-92). In another preferred embodiment. PGCs were collected from the germinal crescent by mechanical dissection of chicken embryo or from the gonads. However, as discussed above, others methods for isolating PGCs are known and can alternatively be used.

By "complete culture medium", it is meant a basal medium, preferably a basal synthetic medium, supplemented with at least one growth factor and animal serum. Example of complete culture medium is described in WO03/076601, WO05/007840, EP787180, U.S. Pat. No. 6,114,168, U.S. Pat. No. 5,340,740, U.S. Pat. No. 6,656,479, U.S. Pat. No. 5,830, 510 and in a Pain of al. (1996, Development 122:2339-2348). According to the invention, "basal medium" meant a medium with a classical media formulation that allows, by itself, at least cells survival, and even better, cell growth. Examples of basal media are BME (basal Eagle Medium), MEM (minimum Eagle Medium), medium 199, DMEM (Dulbecco's modified Eagle Medium), GMEM (Glasgow modified Eagle medium), DMEM-HamF12. Ham-F12 and Ham-F10, Iscove's Modified Dulbecco's medium, MacCoy's 5A medium, RPMI 1640. Basal medium comprises inorganic salts (for examples: $CaCl_2$, $KCl$, $NaCl$, $NaHCO_3$, $NaH_2PO_4$, MgSO$_4$, . . . ), amino-acids, vitamins (thiamine, riboflavin, folic acid, D-Ca panthothenate, . . . ) and others components such as glucose, beta-mercapto-ethanol, sodium pyruvate. Preferably basal medium is a synthetic medium. Most preferred basal medium of the invention is DMEM-HamF12 that are complemented with 2 mM L-glutamin, 1 mM sodium pyruvate, 1% non-essential amino-acids, 0.16 mM beta-mercapto-ethanol.

Alternatively, the complete culture medium is a conditioned medium, preferably BRL conditioned medium. By way of example, BRL conditioned media is prepared according to art-recognized techniques, such as described by Smith and Hooper (1987, Dev. Biol. 121: 1-9). BRL cells are available from ATCC accession number CRL-1442. Conditioned medium may be supplemented with exogenous growth factors as described below.

The term "growth factor" as used herein meant exogenous growth factor added to the culture medium necessary for the survival and the growth of the avian cells in culture. It is possible to schematically distinguish two families of growth factors: the cytokines and the trophic factors. The cytokines are mainly cytokines whose action is through a receptor which is associated with the gp130 protein. Thus, leukemia inhibitory factor (LIF), interleukin 11, interleukin 6, interleukin 6 receptor, Ciliary Neurotrophic factor (CNTF), oncostatin and cardiotrophin have a similar mode of action with the recruitment at the level of the receptor of a specific chain and the combination of the latter with the gp130 protein in monomeric or sometimes hetero-dimeric form. The trophic factors are mainly Stem cell Factor (SCF), Insulin Growth factor 1 (IGF-1) and Fibroblast Growth Factor (FGF), preferably basic FGF (bFGF) or human FGF (hFGF).

The complete culture medium used in step a) of the process of invention comprises basal medium, preferably basal synthetic medium, and at least one cytokine whose action is through a receptor which is associated with the gp130 protein and/or at least one trophic factors. Preferably, the complete culture medium according to the invention comprises basal medium and at least one growth factor selected in the group consisting of Leukemia Inhibitory factor (LIF), oncostatin, cardiotrophin, Insulin Growth factor 1 (IGF-1), Ciliary Neurotrophic factor (CNTF), Interleukin 6 (IL-6), interleukin 6 receptor (IL-6R), Stem cell Factor (SCF), Fibroblast Growth Factor (FGF), interleukin 11 (IL-11).

According to a first preferred embodiment, the complete culture medium is basal medium supplemented with animal serum and with at least IGF-1 and CNTF.

According to a second preferred embodiment, the complete culture medium is basal medium supplemented with animal serum and at least IGF-1, CNTF, IL-6 and IL-6R.

According to a third preferred embodiment, the complete culture medium is basal medium supplemented with animal serum and at least IGF-1, CNTF, IL-6, IL-6R, SCF, FGF.

According to another embodiment, the complete culture medium is a conditioned culture medium comprising growth factors (i.e expressed by BRL cells for example) and optionally supplemented with at least one exogenous growth factors selected in the group comprising: Leukemia Inhibitory factor (LIF), Insulin Growth factor 1 (IGF-1), Ciliary Neurotrophic factor (CNTF), interleukin 6 (IL-6), interleukin 6 receptor (IL-6R), Stem cell Factor (SCF), Fibroblast Growth Factor (FGF), interleukin 11 (IL-11).

The concentration of growth factors IGF-1, CNTF, IL-6, IL-6R, SCF, FGF, IL-11 in the basal medium or in the conditioned culture medium is comprised between about 0.01 to 10 ng/ml, preferably, 0.1 to 5 ng/ml, and more preferably about 1 ng/ml.

The avian embryonic stem cells of the invention are cultured on a layer of feeder cells. Feeder cells can either be cells or cell lines cultured for the purpose of obtaining ES cells. Alternatively, the feeder cells could be substituted with extra-cellular matrix plus bound growth factors. Feeder matrix will thereafter refers to either feeder cells or extra-cellular matrix. A feeder matrix as used herein is constructed in accordance with procedures known in the art. As noted above, it is preferred that the feeder matrix be preconditioned. By the term "preconditioned" it is meant that the feeder matrix is cultured in the presence of media for a period of time prior to the depositing of cells originating from the blastoderm disk fertilized avian eggs in contact with the feeder matrix, e.g. a time sufficient to initiate and establish production of, for example, growth factors or other factors by the feeder matrix; usually a feeder matrix is preconditioned by culturing the feeder matrix by itself for one to two days prior to the depositing of cells originating from the blastoderm disk fertilized avian eggs in contact with the feeder matrix. The feeder cells preferably comprises mouse fibroblast cells. STO fibroblasts are preferred, but primary fibroblasts are also suitable. Also while the present invention has been described with respect to the use of mouse cell feeder matrices, it is contemplated that feeder matrices comprising cells from other murine species (e.g. rat); other mammalian species (e.g; ungulate, bovine, porcine species); or avian species (e.g. Gallinacea, chicken, turkey, duck, goose, quail, pheasant) may also be used. In another embodiment, feeder cells of the invention may be transfected with expression vector(s) allowing for example the constitutive expression of growth factors such as avian SCF in STO cells. Thus, this "feeder" produces the factor in a form which is soluble and/or attached in the plasma membrane of the cells. Thus, the culturing process of the present invention may optionally comprise establishing a monolayer of feeder cells. Feeder cells are mitotically inactivated using standard techniques. For example, the feeder cells may be exposed to X or gamma radiation (e.g. 4000 Rads of gamma radiation) or may be treated with Mitomycin C (e.g. 10 μg/ml for 2-3 hours). Procedures for mitotically inactivating cells are also detailed in the information typically sent with cells from the American Type Culture Collection (ATCC), University Boulevard, Manassas, Va. 20110-2209 (e.g. STO feeder cells are available under ATCC accession number 1503). Mono-layers may optionally be cultured to about 80% confluency, preferably to about 90% confluency, and more preferably about 100% confluency. While configuration of the feeder cells as a monolayer is the preferred configuration for the culture, any suitable configuration is contemplated to be within the scope of the present invention. Thus, for example, layers, mono-layers, clusters, aggregates or other associations or groupings of feeder cells are contemplated to fall within the scope of the present invention and are particularly contemplated to fall with the meaning of the term "matrix".

The culture medium of the invention is supplemented with animal serum. The animal serum preferably used is fetal animal serum. Fetal bovine serum is preferred. Also while the present invention has been described with respect to the use of fetal bovine serum, it is contemplated that animal serum comprising serum from other animal species (e.g. chicken, horse, porcine, ungulate, etc. . . . ) may also be used. The final concentration of animal serum in the culture medium is comprises between approximately 1 to 25%, preferably between 5% to 20%, more preferably between 8% and 12%. In the preferred embodiment, the final concentration of animal serum in the culture medium is approximately 10%. According to a preferred embodiment, the culture medium comprises approximately 10% of fetal calf serum. The culture medium of the invention may comprise in addition antibiotics, such as for example penicilline and streptomycine, to prevent bacterial contamination.

According to another embodiment, the invention provides a method of genetically modifying avian embryonic stem cells, comprising the steps of
  a) transfecting ES cells obtained and cultured according to the method above, with a vector;
  b) selecting transfected ES cells, preferably by addition of a selection agent in the medium, such as for example antibiotics, amino-acids, hormones.
  c) screening and amplification of resistant ES clones genetically modified,
  d) culturing said genetically modified ES cell of step c) on a layer of feeder cells in a culture medium as previously described. According to a first embodiment, said culture medium of step d) comprises animal serum and at least one growth factor selected in the group comprising IGF1, CNTF, IL-6, IL-6R, Il-11, LIF, FGF, SCF, oncostatin, cardiotrophin. According to a preferred embodiment, said culture medium of step d) comprises animal serum and IGF1 and CNTF. According to another embodiment, said culture medium of step d) comprises animal serum and IGF1 and CNTF and optionally at least one growth factor selected in the group comprising IL-6, IL-6R, Il-11, LIF, FGF, SCF, oncostatin and cardiotrophin. According to a third preferred embodiment, said culture medium of step d) comprises animal serum and IGF1, CNTF, IL-6 and IL-6R. According to a fourth preferred embodiment, said culture medium of step d) comprises animal serum and IGF1, CNTF, IL-6, IL-6R, SCF and FGF.

ES cells of step c) are genetically modified. Genetic modification are performed either by transient or stable transfection with the vector in ES cells. According to a preferred embodiment the ES are stably transfected with the vector according to techniques well known by the man skilled in the Art. According to a first embodiment, the vector is inserted randomly into the genome of ES cells. According to a preferred embodiment, the vector is inserted by homologous recombination into the genome of ES cells. WO03/043414 described protocols and expression vectors to genetically modified ES cells by homologous recombination.

ES cells of step a) may be maintained and cultured for a long period of time in vitro prior to their introduction into recipient embryo. This long period of time allows to genetically modified said cells. According to a preferred embodiment, the cells have been in vitro cultured for at least 5 days, at least 10 days, at least 14 days, at least 25 days, at least 50 days, at least 75 days, at least 100 days.

The terms "vector" as used herein refer to a natural or synthetic single or double stranded plasmid or viral nucleic acid molecule that can be transfected into cells and replicate independently of, or within, the host cell genome. A circular double stranded plasmid can be linearized by treatment with an appropriate restriction enzyme based on the nucleotide sequence of the plasmid vector. A nucleic acid can be inserted into a vector by cutting the vector with restriction enzymes and ligating the pieces together. The nucleic acid molecule can be RNA or DNA. The term "plasmid" as used herein refers to a small, circular DNA vector capable of independent replication within a bacterial or yeast host cell. The nucleic acid vector further includes at least one regulatory sequence operably linked to a nucleotide sequence coding for a "polypeptide of interest". Regulatory sequences are well recognized in the art and may be selected to ensure good expression of the linked nucleotide sequence without undue experimentation by those skilled in the art. As used herein, the term "regulatory sequences" includes promoters, enhancers, and other elements that may control expression. Standard molecular biology textbooks such as Sambrook et al. eds "Molecular Cloning: A Laboratory Manual" 2nd ed. Cold Spring Harbor Press (1989) and Lodish et al. eds., "Molecular Cell Biology," Freeman (2000) may be consulted to design suitable expression vectors, promoters, and other expression control elements. It should be recognized, however, that the choice of a suitable expression vector depends upon multiple factors including the choice of the host cell to be transformed and/or the type of protein to be expressed. Also useful for various applications are tissue-selective (i.e. tissue-specific) promoters, i.e., promoters from which expression occurs preferentially in cells of a particular kind of tissue, compared to one or more other types of tissue. An exemplary tissue-specific promoter is a chicken oviduct-specific promoter that is naturally associated with the proteins of avian egg whites including ovalbumin, lysozyme, ovomucoid, conalbumin and ovomucin and the like. Useful promoters also include exogenously inducible promoters. These are promoters that can be "turned on" in response to an exogenously supplied agent or stimulus, which is generally not an endogenous metabolite or cytokine. Examples include an antibiotic-inducible promoter, such as a tetracycline-inducible promoter, a heat-inducible promoter, a light-inducible promoter, or a laser inducible promoter. (e.g., Halloran et al., 2000. Development 127(9): 1953-1960; Gerner et al., 2000, Int. J. Hyperthermia 16(2): 171-81; Rang and Will, 2000, Nucleic Acids Res. 28(5): 11205; Hagihara et al., 1999, Cell Transplant. 8(4): 4314; Huang et al., 1999, Mol. Med. 5(2): 129-37; Forster, et al., 1999, Nucleic Acids Res. 27(2): 708-10; and Liu et al., 1998. Biotechniques 24(4): 624-8, 630-2 (1998)). As used herein the term "polypeptide of interest" or "protein of interest" refer to a polymer of amino acids of three or more amino acids in a serial array, linked through peptide bonds. The term "polypeptide" includes proteins, protein fragments, protein analogues, oligo-peptides, peptides and the like. The term "polypeptide" contemplates polypeptides as defined above that are encoded by nucleic acids, produced through recombinant technology, isolated from an appropriate source or are synthesized. Non limiting examples of polypeptides are growth hormones, cytokine, interleukine, interferon, enzymes, immunoglobulins or fragments thereof. The terms "transfection" or "transfected" as used herein refer to the process of inserting a nucleic acid into a host cell (i.e the avian ES). Many techniques are well known to those skilled in the art to facilitate transfection of a nucleic acid into a prokaryotic or eukaryotic organism. These methods involve a variety of techniques including, but not limited to, treating the cells with high concentrations of salt such as, but not only, a calcium or magnesium salt, an electric field (i.e. electroporation), detergent, or liposome mediated transfection (i.e. lipofection, etc.), to render the host cell competent for the uptake of the nucleic acid molecules.

The invention also provide a method of obtaining a chimeric chick comprising the steps of:
  a) introducing avian ES cells obtained and cultured by the method of the invention into the sub-germinal cavity of a recipient avian embryo; and
  b) incubating the embryo obtained in step a) to hatch as a chick;
  c) selecting said chimeric chick comprising heterologous cells having colonized said chick.

The term "chick" as used herein meant a young bird, and it includes young chicken. The term "subgerminal cavity" meant the space between the blastoderm and the yolk. This space is created when the blastoderm cells absorb fluid from the albumin and secrete it between themselves and the yolk.

It is also an object of the invention to provide a method of obtaining a genetically modified chimeric chick comprising the steps of:
- a) introducing genetically modified ES obtained and cultured by the method of the invention into the sub-germinal cavity of a recipient avian embryo; and
- b) incubating the embryo obtained in step a) to hatch as a chick;
- c) selecting said chimeric chick comprising genetically modified heterologous cells having colonized said chick.

The selection of said chimeric chick may be performed either by phenotypic or genotypic analysis. According to a preferred embodiment, the chimeric chick is selected by phenotypic analysis of plumage.

According to another embodiment, the method of obtaining chimeric chick of the invention may comprise the additional step of determining the sex of recipient embryo prior the introduction of ES cells.

According to another embodiment, the recipient embryo derives from a freshly laid un-incubated egg and comprises between around 5,000 to around 70,000 cells. Preferably, said recipient embryo is at stage comprised between stages VI and XII of Eyal-Giladi & Kochav's classification, preferably:
- around the stage X of Eyal-Giladi & Kochav's classification when the embryo is a chicken;
- around the stage VII of Eyal-Giladi & Kochav's classification when the embryo is a Muscovy duck;
- around the stage VIII of Eyal-Giladi & Kochav's classification when the embryo is a Pekin duck;
- around the stage XI of Eyal-Giladi & Kochav's classification when the embryo is a Japanese quail or a goose;
- around the stage VII-VIII of Eyal-Giladi & Kochav's classification when the embryo is a Guinea fowl or a turkey;

Preferably, at least 1000 ES cells, at least 10,000 ES cells, at least 15,000 ES cells, at least 30,000 ES, at least 45,000 ES cells, at least 65,000 ES cells, at least 85,000 ES cells or at least 100,000 ES cells are introduced into the sub-germinal cavity of the recipient avian embryo. According to a preferred embodiment, at least 30,000 ES cells are introduced into the sub-germinal cavity of the recipient avian embryo.

ES cells introduced into the sub-germinal cavity of the recipient avian embryo may be a mixed population of female and male ES cells. According to another embodiment, the recipient embryo and donor ES cells are previously sexed before introduction. According to a preferred embodiment, female ES cells are introduced into the sub-germinal cavity of a female recipient avian embryo. According to another preferred embodiment, male ES cells are introduced into the sub-germinal cavity of a male recipient avian embryo.

The method of obtaining chimeric chick of the invention comprises the optional step of slightly irradiating the recipient embryo with X or gamma irradiation prior to the introduction of ES cells into the sub-germinal cavity of said recipient embryo. According to a preferred embodiment, the chicken recipient embryo is irradiated with between 3 to 6 gray of X rays, preferably around 4 gray of X-rays. According to a preferred embodiment, around 15,000 chicken ES cells are introduced into the sub-germinal cavity of the recipient chicken embryo, previously X-irradiated with around 4 gray. According to another preferred embodiment, at least 30,000 chicken ES cells are introduced into the sub-germinal cavity of the a non-irradiated recipient chicken embryo.

According to a first embodiment, the recipient chicken embryo is of White Leghorn strain and the donor chicken ES cells derived from a strain selected in the group composed of barred rock strain, Marans strain, S86N strain. According to second embodiment, the recipient chicken embryo is of a chicken strain selected in the group comprising barred rock strain, Marans strain and S86N strain and the donor chicken ES cells derived from White Leghorn strain.

The selection of the chimeric chick of the invention comprising heterologous cells comprises the steps of:
- a) obtaining a sample of genetic material from said chimeric chick;
- b) assaying for the presence of a polymorphism in a sequence of avian leucosis virus integrated in the avian genome, and wherein the polymorphism is identifiable by an amplification by a set of primers selected in the group consisting of the set of a forward primer 5'-GGTGTAAATATCAAAATTATC-3' (SEQ ID n° 1) and a reverse primer 5'-CGGITAAAATACGAATAGAGA-3' (SEQ ID N° 2) and the set of a forward primer 5'-CTATGAGCAGTTACGAGGGTC-3' (SEQ ID N° 3) and a reverse primer 5'-CGGACCAACAGGCTAGTCTC-3' (SEQ ID N° 4). According to a preferred embodiment, said chicken ES cells are derived from barred rock species and said recipient embryo is of White Leghorn species. Said amplification is performed by polymerase chain reaction (PCR) or reverse-transcriptase PCR and wherein said analysis comprises the digestion of PCR amplified DNA with the restriction enzyme HincII.

The method of identifying the presence or absence of a polymorphism is selected from a group consisting of: restriction fragment length polymorphism (RFLP) analysis, heteroduplex analysis, single strand conformational polymorphism (SSCP), denatu rating gradient gel electrophoresis (DGGE) temperature gradient gel electrophoresis (TGGE), allele-specific oligonucleotide (ASO) an dideoxy-fingerprinting (ddF).

The step of assaying for the presence of said polymorphism comprise the steps of:
- a) digesting said genetic material with HincII restriction enzyme;
- b) separating the fragments obtained from said digestion;
- c) detecting the restriction pattern generated by said fragments; and
- d) optionally comparing said pattern with at least one restriction pattern obtained by digestion of White Leghorn, Marans, Barred Rock, S86N genetic material using HincII restriction enzyme, wherein difference in restriction patterns detected in step c) and d) is indicative of chimeric chick comprising heterologous cells.

The invention also includes the method of obtaining a progeny of the chimeric chick wherein said method comprises the following steps:
- a) allowing the selected chimeric chick obtained by the method of the invention to mature as an adult bird;
- b) breeding said adult bird having heterologous cells herein, thereby producing a bird progeny; and
- c) selecting the birds in the progeny comprising heterologous cells. The selection of said birds may be performed by phenotypic analysis of plumage or when possible by genotypic analysis by assaying for the presence of a HincII polymorphism in a sequence of avian leucosis virus integrated in the bird genome.

The method may comprise the additional step of expressing the heterologous polypeptide encoded by the vector comprised in genetically modified heterologous cells. Preferably, the heterologous polypeptide is delivered into biological fluids of the bird, such as blood, sperm, urine, or the white of a developing avian egg produced by a female of the genetically modified bird.

The present invention also relates to a culture medium for genetically and non-genetically modified avian embryonic stem (ES) cells, preferably chicken and duck ES cells, supplemented with animal serum and comprising at least one growth factors selected in the group consisting of insulin-like growth factor-1 (IGF-1), ciliary neurotrophic factor (CNTF), Interleukin 6 (Il-6), Interleukin 6 receptor (Il-6R), interleukin 11. Stem cell factor (SCF), fibroblast growth factor (FGF), leukaemia inhibitory factor (LIF), oncostatin and cardiotrophin wherein said medium is sufficient for the maintenance of said chicken embryonic stem cells into culture for 10 days at least, for 30 days at least, preferably for 100 days at least and more preferably for infinite period.

According to a preferred embodiment, the present invention also relates to a basal culture medium for genetically or non-genetically modified avian embryonic stem (ES) cells, preferably chicken and duck ES cells, supplemented with animal serum and supplemented with insulin-like growth factor-1 (IGF-1) and ciliary neurotrophic factor (CNTF).

According to a second preferred embodiment, the present invention relates to a basal culture medium for genetically or non-genetically modified avian embryonic stem (ES) cells, preferably chicken and duck ES cells, supplemented with animal serum and supplemented with insulin-like growth factor-1 (IGF-1), ciliary neurotrophic factor (CNTF), Interleukin 6 (Il-6) and Interleukin 6 receptor (Il-6R).

According to a third preferred embodiment, the present invention relates to a basal culture medium for genetically or non-genetically modified avian embryonic stem (ES) cells, preferably chicken and duck ES cells, supplemented with animal serum and supplemented with insulin-like growth factor-1 (IGF-1), ciliary neurotrophic factor (CNTF), Interleukin 6 (Il-6), Interleukin 6 receptor (Il-6R), Stem cell factor (SCF), Fibroblast growth factor (FGF).

Said media are sufficient for the maintenance of said avian embryonic stem (ES) cells, preferably chicken and duck ES cells into culture for at least 7 days, for at least 14 days, for at least 30 days, for at least 50 days, and preferably for at least 100 days.

The culture medium of the invention may further comprise optionally at least one compound selected in the group comprising Interleukin-11, cardiotrophin, oncostatin and/or LIF. The culture medium of the invention may further comprise a layer (i.e lawn) of feeder cells.

The invention also provides a method of genetic polymorphism analysis to distinguish between White Leghorn chicken strain from another chicken strain, wherein said method comprises the steps of:
 a) obtaining a sample of genetic material from said White Leghorn chicken strain, and a sample of genetic material from said other chicken strain;
 b) assaying for the presence of a polymorphism in a sequence of avian leucosis virus integrated in the chicken genome, and wherein the polymorphism is identifiable by an amplification by a set of primers selected in the group consisting of the set of a forward primer 5'-GGTGTAAATATCAAAATTATC-3' (SEQ ID n° 1) and a reverse primer 5'-CGGTTAAAATAC-GAATAGAGA-3' (SEQ ID N° 2) and the set of a forward primer 5'-CTATGAGCAGTTACGAGGGTC-3' (SEQ ID N° 3) and a reverse primer 5'-CGGACCAA-CAGGCTAGTCTC-3' (SEQ ID N° 4).

In the method of genetic polymorphism analysis according to the invention, the amplification is preferably performed by polymerase chain reaction (PCR) or reverse-transcriptase PCR. The step of assaying for the presence of said polymorphism comprises the steps of:
 a) digesting PCR amplified DNA with the HincII restriction enzyme;
 b) separating the fragments obtained from said digestion;
 c) detecting the restriction pattern generated by said fragments; and
 d) comparing said pattern obtained by digestion of White Leghorn genetic material using HindIII restriction enzyme and said pattern obtained by digestion of genetic material of said other chicken strain, wherein the presence of HincII restriction site is indicative of White Leghorn strain, and the absence of HincII restriction site is indicative that it is not a White Leghorn strain.

The method of identifying the presence or absence of a polymorphism is selected from a group consisting of: restriction fragment length polymorphism (RFLP) analysis, heteroduplex analysis, single strand conformational polymorphism (SSCP), denaturating gradient gel electrophoresis (DGGE), temperature gradient gel electrophoresis (TGGE), allele-specific oligonucleotide (ASO) an dideoxy-fingerprinting (ddF).

The examples below explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims. For the remainder of the description, reference will be made to the legend to the figures below.

FIGURES

FIG. 1: cell culture kinetics of avian ES cells

Chicken ES cells were grown on a mouse feeder layer in culture medium supplemented with 10% fetal calf serum and with IGF1, CNTF, IL6, IL6R, SCF, FGF.

Number of cells was determined at each dissociation. Numbers of cells obtained at each dissociation were added to determine the cumulative coefficient of proliferation FIG. 2: Morphology of chicken ES cells Morphologies of blastodermal cells:
(A) BR22p2 and (B) BR22p3: round-shaped cells with big nucleus and small cytoplasm.
(C) BR29p12: dispersed with looser connections blastodermal cells.

Figure 3:
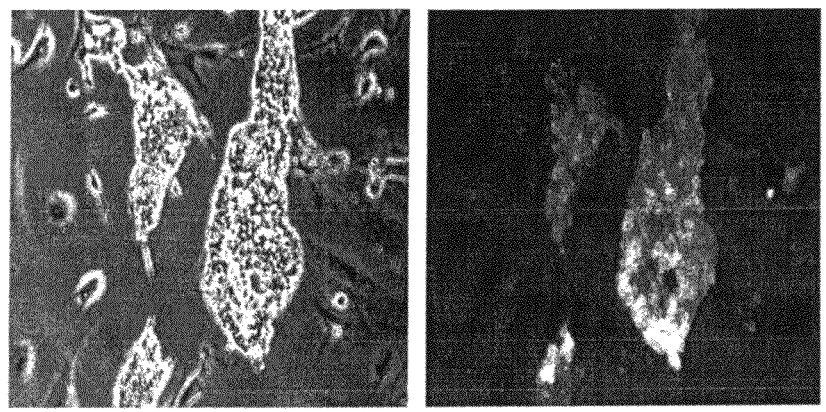

FIG. 3: Expression of cell-specific marker SSEA-1

Expression of ES cell-specific markers SSEA-1 was tested on blastodermal cells maintained in vitro for different culture period. Left panel A: phase contrast. Right panel B: antibody staining.

Figure 4:
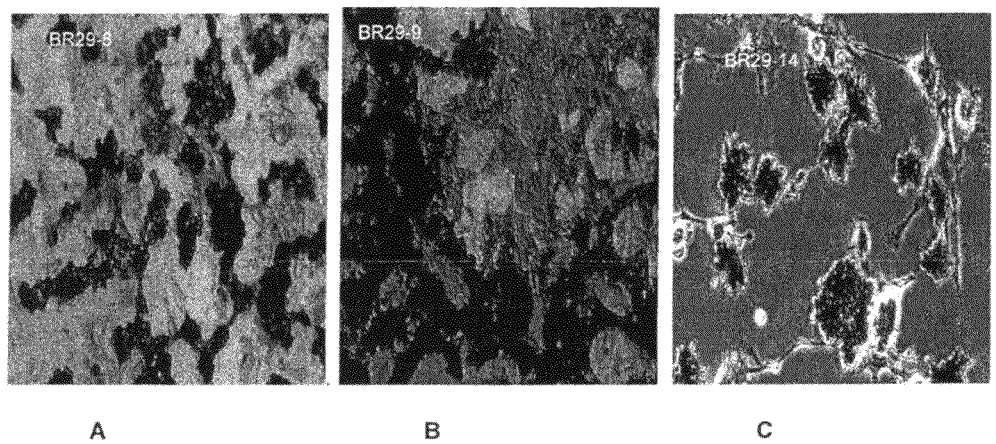

FIG. 4: Alcaline phosphatase activity of ES cells

Endogenous alkaline phosphatase activity of blastodermal cells. Cells were stained for alkaline phosphatase activity for different culture period.

Figure 5:
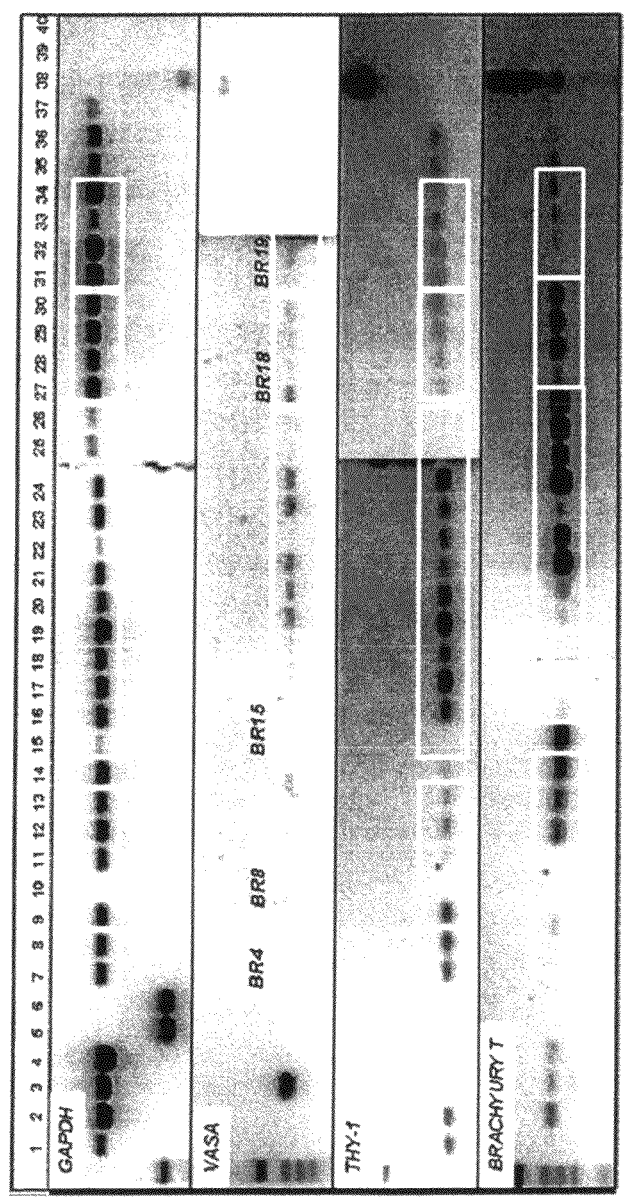

FIG. 5: Evolution of expression of markers of differentiation VASA, THY1, BRACHYURY while cells are maintained in culture.

Markers and culture. 1: Bone Marrow, 2: Embryo (head); 3: Male gonads, 4: embryo (stade X); 5: feeder (STO); 6: feeder (SN); 7: BR 4-5; 8: BR4-6; 9: BR 5-2; 10: BR 8-7; 11: BR 8-8; 12: BR 8-9; 13: BR 8-12; 14: V 9-19; 15: BR 15-0; 16: BR 15-1; 17: BR 15-2; 18: BR 15-3; 19: BR 15-5; 20: BR 15-6; 21: BR 15-7; 22: BR 15-8; 23: BR 15-8; 24: BR 15-9; 25: BR 15-10; 26: BR 15-11; 27: BR 18-2; 28: BR 18-3; 29: BR 18-4; 30: BR 18-5; 31: BR 19-1; 32: BR 19-2; 33: BR 19-3; 34: BR 19-4; 35: BR 20-2; 36: BR 20-3; 37: S1 p20; 38: gDNA Barred Rock; 39: water; 40: water.

Expression of Vasa. Thy-1 and Brachuyry (T) markers during different culture period. GAPDH control marker. Cells were maintained in culture for several weeks. Cell pellets were frozen at each dissociation. RNA extraction and RT-PCR were performed concomitantly for each cell pellets.

Figure 6:
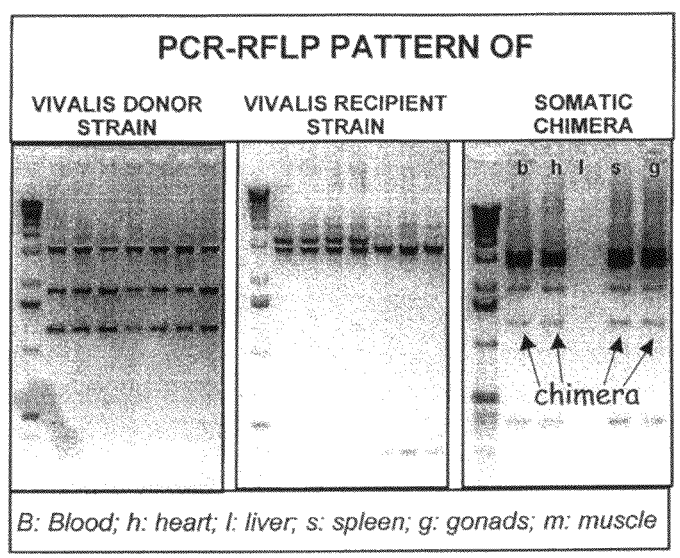

FIG. 6: PCR RFLP profile analysis of the donor and recipient chicken strains and of a chimera PCR RFLP profile of the donor and recipient chicken strains and of a chimera. 7 embryonated freshly laid eggs from donor and recipient chicken strains were incubated for 5 days. DNA was extracted from total embryos Somatic chimera: embryo injected with donor cells were incubated for 18 days. DNA was extracted from blood, heart, liver, spleen and gonads.

Figure 7:
Figure 7:
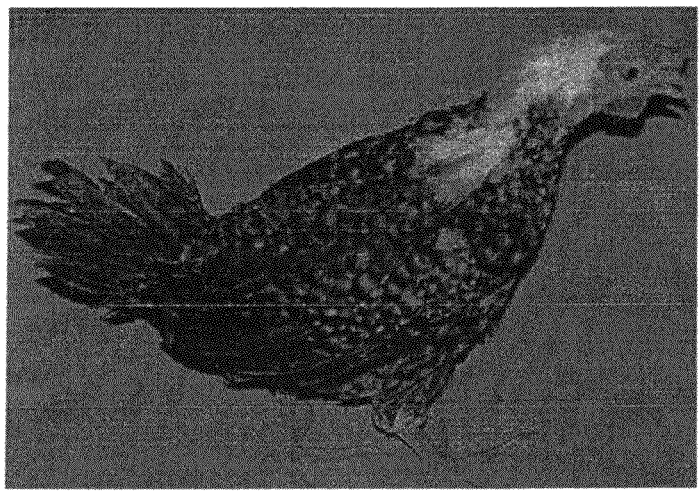

FIG. 7: Chimera Birds

Donor chicken cells were injected into recipient chicken embryos. Recipient embryos were incubated until hatch. Chimeric birds were raised until adulthood.

Figure 8:
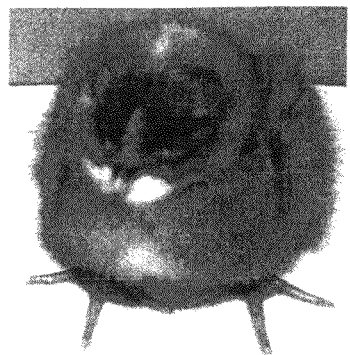
Figure 8:

FIG. 8: F1 and F2 progeny

8A: F1 Bird with a typical Barred-Rock plumage pigmentation

8B: F2 birds from 5664-5665 hen. Hens were inseminated with semen from Barred Rock roosters. Eggs were incubated until hatch.

Figure 9:
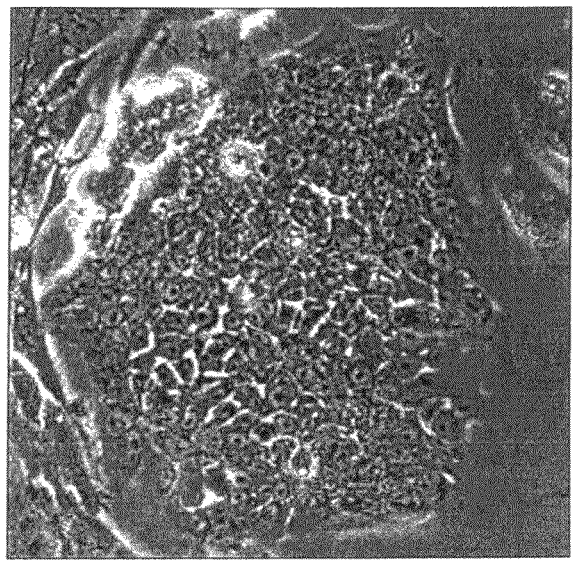

FIG. 9: Morphology of duck ES cells

Duck ES cells were grown on a mouse feeder layer in DMEM culture medium supplemented with 10% fetal calf serum and with IGF1, CNTF, IL6, IL6R, SCF, FGF.

EXAMPLES

Example 1

Materials and Methods

Blastodermal Cells

Embryos were collected from freshly laid un-incubated eggs. A sterile filter paper ring was laid over the embryo with blastodisc in center of cutout area. The yolk membrane was cut around outside of the disk. The disk was flipped over and transfer to a petri dish of PBS at room temperature. Excess yolk was carefully washed out. The entire blastoderm was removed by gentle aspiration with a Pasteur pipette and transfer in PBS. An average of 200 embryos was pooled together. The cells were centrifuged twice at 300 g. The cell pellet was mechanically dissociated in culture medium. Cells in complete culture medium were seeded on an inactivated STO feeder layer. Blastodermal cells were maintained at 39° C. in 7.5% $CO_2$. The cells were dissociated by incubation at 39° C. in a solution of pronase (5 to 2 w/v). Dissociated cells were seeded on new feeder layer cells in the complete medium. Between passages 3 and 5 cells were seeded in the minimal medium, on a STO feeder layer.

Culture Medium

The complete culture medium was composed of DMEM-F12 base supplemented with 10% foetal calf serum (JRH), 0.16 mM beta-mercaptoethanol (SIGMA), 1% non essential amino acids (Biowhittaker), 1 mM sodium pyruvate (Biowhittaker), 2 mM L-Glutamine (Biowhittaker), 1 ng/ml IGF1 (Tebu), 1 ng/ml CNTF (Eurobio), 1 ng/ml Il-6 (Eurobio), 1 ng/ml Il-6R (Tebu), 1 ng/ml SCF (Tebu), 1 ng/ml bFGF (Peprotech), 1% penistreptomycine (Biowhittaker).

Alternatively, the complete culture medium was composed of DMEM-F12 base supplemented with 10% foetal calf serum (JRH), 0.16 mM b-mercaptoethanol (SIGMA), 1% non essential amino acids (Biowhittaker), 1 mM sodium pyruvate (Biowhittaker), 2 mM L-Glutamine (Biowhittaker), 1 ng/ml IGF1 (Tebu), 1 ng/ml CNTF (Eurobio), 1 ng/ml Il-6 (Eurobio), 1 ng/ml Il-6R (Tebu), 1% penistreptomycine (Biowhittaker).

Alternatively, the complete culture medium may also be composed of DMEM-F12 base supplemented with 10% foetal calf serum (JRH), 0.16 mM b-mercaptoethanol (SIGMA), 1% non essential amino acids (Biowhittaker), 1 mM sodium pyruvate (Biowhittaker), 2 mM L-Glutamine (Biowhittaker), 1 ng/ml IGF1 (Tebu), 1 ng/ml CNTF (Eurobio), 1% penistreptomycine (Biowhittaker).

Preparation of Feeder Cells

The mouse fibroblast STO cell line (ATCC) was maintained at 37.5° C., 7.5% $CO_2$ in DMEM (Cambrex) supplemented with 4% foetal calf serum (JRH) and 1% glutamine (Biowhittaker). At sub-confluence STO cells were dissociated with pronase (Roche) 1×, washed with PBS and irradiated with a gamma source at 45 grays. Feeder cells were seeded at $1.5 \times 10^6$ to $2 \times 10^6$ cells in fresh medium in 100-mm dishes.

Transfection

STO cell lines: pGPARα and pMEHCS were given by Dr. Bertrand Pain. pCINeo was purchased from Promega. Plasmid DNA was prepared using alkaline lysis and PEG purification. For transfection, cells were seeded in the morning at $0.5 \times 10^6$ cells per 100-mm dish. They were transfected in the evening with 3.0 µg of circular pCINeo, 15 µg pGPARα or pMEHCS using FuGENE 6 (Roche) lipofectant. The day after, cells were washed and the medium was changed. Selection with neomycine, 0.3 mg/ml began at D1 and was applied for 8 days. Resistant cells were amplified and frozen in liquid nitrogen.

Alkaline Phosphatase Reaction:

Cells were washed twice with PBS and fixed in 1.5% formaldehyde, 0.5% glutaraldehyde, 0.1% Igepal for 10 to 20 minutes at 4° C. After washing cells were incubated at 37° C. in the alkaline phosphatase staining solution composed of 100 mM NaCl, 100 mM Tris pH 9.5, 50 mM $MgCl2$, 1 mg/ml NBT, 0.1 mg/ml BCIP. The reaction was stopped by addition of PBS 1× or H2O.

Immunofluorescence Analysis:

SSEA-1 antibodies were purchased from the Developmental Studies Hybridoma Bank of the University of IOWA.

Cells were fixed either 20 minutes at 4° C. in 1.5% formaldehyde, 0.5% glutaraldehyde, or in 0.2% glutaraldehyde, 0.01% IGEPAL, or 10 minutes at room temperature in paraformaldehyde 4% or methanol.

Cells were incubated in PBS-BSA 0.1% for 2 h to 4 h. The first diluted antibody was added overnight. After washing, the second FITC-labelled anti-IgG antibody was added for 1 h at 4° C. Reaction was stopped by removing the antibody and washing the cells with PBS. Cells were observed with a fluorescent microscope.

PCR RFLP:

DNAs from tissues of embryos incubated for 18 days were purified according to the instructions of QIAamp DNA minikit. A fragment of avian leucosis virus integrated in the genome was amplified by PCR using the following couples of primers:

```
Oligos (157-158):
Forward:  5'-GGTGTAAATATCAAAATTATC   (SEQ ID N° 1)

Reverse:  5'-CGGTTAAAATACGAATAGAGA   (SEQ ID N° 2)

Oligos (78-81):
Forward:  5'-CTATGAGCAGTTACGAGGGTC   (SEQ ID N° 3)

Reverse:  5'-CGGACCAACAGGCTAGTCTC    (SEQ ID N° 4)
```

Amplicons are respectively 3106 and 1004 bp. The specificity of primer 157 is higher for DNA from Barred Rock chicken than DNA from White Leghorn. The resulting amplicons are cut with the HincII enzyme.

RT PCR Analysis:

RNAs were purified according to the instructions of Promega SV total RNA isolation kit. Head RNA were extracted from embryos after 5 days of incubation, bone marrow from thighbone embryos incubated for 15 days, testis from adult chicken. RNA from BR15 cells was extracted according to the instructions of Qiagen RNeasy kit. RNAs were reverse transcribed according to Promega Random primers and AMV Reverse transcriptase kits' instructions. PCR amplification was realized using the following primers.

```
Oligos vasa:
Vasa forward:
TTTGGTACTAGATGAAGCAGACC       (SEQ ID N° 5)

Vasa reverse:
GTTCCCTATCTCCATGAATGC         (SEQ ID N° 6)

Oligos Brachyury:
Brachyury forward:
CACAAAGACATGATGGAGGAAG        (SEQ ID N° 7)

Forward 2:
TGAAGTCCTCTCCAAAACCATT        (SEQ ID N° 8)

Brachyury reverse:
CATAAGTTCGGGTACTGACTGG        (SEQ ID N° 9)

Reverse 2:
CACAAAATCATTCTGCGGTAAA        (SEQ ID N° 10)

Oligos GAPDH:
GAPDH forward:
AGGTGCTGAGTATGTTGTGGAGTC      (SEQ ID N° 11)

GAPDH reverse:
AGAACTGAGCGGTGGTGAAGA         (SEQ ID N° 12)

Oligos Thy-1:
Forward:
AGGACAACAGGAAGCACATCAT        (SEQ ID N° 13)

Reverse:
GTTCTGGATCAAGAGGCTGAAG        (SEQ ID N° 14)
```

Cells Injections into Recipient Embryos:

When irradiated, recipient embryos were prepared by exposing freshly laid, un-incubated eggs to 4 Grays of X irradiation from an accelerator source. The embryos were accessed through a window cut into the long axis of the egg. The shell was removed by grinding. The shell membrane was maintained wet by addition of a drop of PBS. The shell membrane was cut to expose the embryo just before the injection of cells. 3 μl of cells in culture medium were injected into the sub-germinal cavity of the recipient embryo using a micropipette.

The window was closed by aligning two pieces of shell membrane previously dipped into albumen. When the shell membranes were dried the windows were tightly sealed with surgical tape. Eggs were incubated in conventional incubators maintained at 37.5° C. and 50% relative humidity and turned through 90° every hour for 18 days. Eggs were then transferred to a conventional hatcher at 37° C. and 85% relative humidity until hatch. Phenotypic and somatic chimerism were evaluated in embryos after 18 days of incubation. Germline contribution of donor cells was assessed by mating injected birds to Barred Rock chickens.

Example 2

Isolation and Amplification of Chicken ES Cells

Chicken embryonic Stem cells were isolated from freshly laid eggs. An average of 200 embryos were pooled together and seeded on a feeder layer of irradiated mouse fibroblasts. Actually, Etches et al. (1996 Mol. Reprod. Dev. 45:291-288), had demonstrated that significantly more somatic chimeras were observed following the injection of chicken blastodermal cells co-cultured with mouse fibroblasts. From initial seeding to passages 3 to 5, blastodermal cells were grown in the complete culture medium composed of DMEM-F12 base supplemented with 10% foetal calf serum (JRH), 0.16 mM beta-mercaptoethanol (SIGMA), 1% non-essential amino acids (Biowhittaker), 1 mM sodium pyruvate (Biowhittaker), 2 mM L-Glutamine (Biowhittaker), 1 ng/ml IGF-1 (TEBU), 1 ng/ml CNTF (Eurobio), 1 ng/ml IL-6 (Eurobio), 1 ng/ml IL-6R (TEBU), 1 ng/ml SCF (TEBU), 1 ng/ml bovine FGF (Peprotech), 1% penistreptomycine (Biowhittaker). Then after several passages, some growth factors were removed and cells were grown in minimal culture medium to avoid differentiation. The growth factors that were removed are either (SCF and FGF), or (SCF, FGF, IL-6, IL-6R).

The culture medium to grow chicken ES cells to avoid differentiation, comprises basal medium (i.e DMEM-F12) supplemented with 10% foetal calf serum (JRH), 0.16 mM beta-mercaptoethanol (SIGMA), 1% non-essential amino acids (Biowhittaker), 1 mM sodium pyruvate (Biowhittaker), 2 mM L-Glutamine (Biowhittaker), and supplemented with 1 ng/ml IGF-1, 1 ng/ml CNTF, 1 ng/ml IL-6, 1 ng/ml IL-6R, 1% penistreptomycine. Alternatively, the culture medium to grow chicken ES cells to avoid differentiation, comprises basal medium (i.e DMEM-F12) supplemented with 10% foetal calf serum (JRH), 0.16 mM beta-mercaptoethanol (SIGMA), 1% non-essential amino acids (Biowhittaker), 1 mM sodium pyruvate (Biowhittaker), 2 mM L-Glutamine (Biowhittaker), and supplemented with 1 ng/ml IGF-1, 1 ng/ml CNTF, 1% penistreptomycine (Biowhittaker).

Chicken ES cells could be isolated and expanded from different chicken strains (table 1).

TABLE 1

Isolation of ES cells from various chicken strains.

| strain | nb of experiments | nb of isolates | % success |
|---|---|---|---|
| S86 N | 127 | 33 | 26 |
| Valo | 17 | 5 | 29 |
| Brown Leghorn | 53 | 4 | 7 |
| GF30 | 20 | 4 | 20 |
| White Leghorn | 14 | 1 | 7 |
| Cou Nu Rouge | 11 | 4 | 36 |

TABLE 1-continued

Isolation of ES cells from various chicken strains.

| strain | nb of experiments | nb of isolates | % success |
|---|---|---|---|
| Marans | 29 | 16 | 55 |
| Barred Rock | 49 | 35 | 72 |
| ISA | 3 | 1 | 33 |

Figure 2:
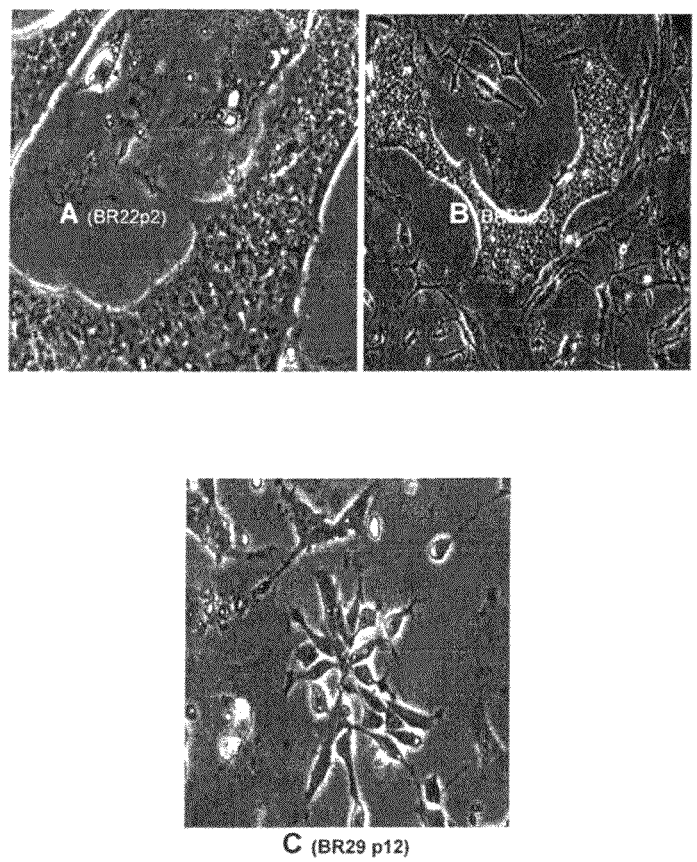

The characterization of the ES status of the in vitro isolated and amplified cells relied on a series of biological criteria that have been demonstrated to be specific for mouse and human ES cells: the self-renewal property, the cell morphology, the expression of stem cells specific markers and the totipotency of the cells, ie. their ability to differentiate in vitro in different lineages and in vivo to contribute to the constitution of an embryo. The growth characteristics of most of the isolates were identical to the ones observed with chicken blastodermal cells maintained for more than a year in culture (FIG. 1), indicating their potentiality of indefinite self renewal. Blastodermal cells grew as colonies. They were round-shaped cells, with a big nucleus and a small cytoplasm (FIG. 2, BR22p2 & BR22p3). Interestingly, it was observed that the morphology of the blastodermal cells evolved during the culture period from tightly connected cells (FIG. 2 BR22p2 & BR22p3) to more dispersed cells with looser connections (FIG. 2, BR29p12). The cells with looser connections could be stabilized on long term culture in the minimum medium. Cells of the different morphologies have been further characterized for the expression of stem cells specific markers and for their ability to contribute to the constitution of an embryo.

ES cells are classically defined by the expression of different markers, ECMA-7 (Kemler et al. 1981 J. Embryol. Exp. Morphol. 64:45-60), SSEA-1 (Solter and Knowles, 1978 Proc. Natl. Acad. Sci, USA 75(11):5565-5569), EMA-1 (Hahnel and Eddy, 1986 J. reprod. Immunol, 10(2)89-110); the presence of specific enzymatic activities, telomerase and alkaline phosphatase activity and by the absence of markers of differentiated cells like TROMA-1. The expression of EMA-1 and SSEA-1 markers and alkaline phosphatase activity was assessed on the in vitro amplified blastodermal cells. The morphology of the blastodermal cells changing during the culture period, markers specific to the germ (Tsunekawa et al, 2000 Development 127:2741-2750), mesoderm (Wilkinson et al, 1990, Nature 343:657-659) and hematopoietic (Uchida at al, 1994 Blood 83:3758-3779) lineages were added to complete the analysis. Since antibodies against Brachyury, Thy-1 and vasa were not available, transcription of corresponding genes was assessed by RT PCR. This analysis was performed throughout an extended culture period and with respect to the different morphologies. SSEA-1 and EMA-1 remained expressed throughout a long culture period (FIG. 3). Alkaline phosphatase activity remained also stable throughout the same culture period (FIG. 4).

FIG. 5 illustrates the evolution of expression of markers of differentiation while cells are maintained in culture. Vasa mRNA was strongly present in male gonads as expected (FIG. 5 lane 3). It was not detected in stage X embryos (lane 4), although germ cells are present in stage X embryos. Vasa gene was weakly but reproducibly expressed in cells maintained in culture (lane 18 to 36). The absence of Vasa transcripts in stage X embryos might be explained by a poor sensitivity of the RT PCR. The expression of vasa gene in cells amplified in vitro might mean either that these cells have germ-line competence or that germ cells, that are present in stage X embryos, have been amplified in vitro. Brachyury mRNA, a marker of mesoderm lineage, was already detected in stage X embryos (embryos from freshly laid eggs) (FIG. 5, lane 4). Expression increased while cells are maintained in culture (FIG. 5, BR8 lane 12 & 13; BR 15 lane 19 to 26; BR18 lane 27 to 30 and BR19 lane 32 to 34). Hematopoietic lineage originated from the mesoderm. Thy-1 mRNA, a marker of the hematopoietic lineage, was also detected in cells maintained in culture (lanes 7, 8; 11, 12, 13; 16 to 24; 27 to 34). HNK1 a marker of neural crest cells in chick was expressed by blastodermal cells. The expression of HNK1 remained stable while cells were maintained in culture (data not shown). Markers of undifferentiated cells were expressed throughout the all culture period (data not shown). Cultured blastodermal cells expressed markers of undifferentiated cells as well as neural crest cells and mesoderm markers. Surprisingly, Vasa gene which was thought to be germ cells specific is transcribed in ES cells.

The totipotency of the in vitro amplified chicken cells was check by evaluating their ability to contribute in vivo to the reconstitution of an embryo.

Experiment were set-up with different number of chicken ES cells injected into a recipient chicken embryo to determine the effects on level of chimerism. The impact of the irradiation of the recipient embryo on the efficiency of colonization has also been studied. Four parameters were selected to monitor the effect of the injections and the radiation: (i) the viability of the embryos; (ii) the percentage of phenotypic chimera (percentage of embryos with colored feathers); (iii) the extend of phenotypic chimerism (percentage of colored feathers); (iv) the percentage of somatic chimerism (chimerism in other tissues than the feather).

300, 5,000, 15,000 or 30,000 ES donor cells were injected in the sub-germinal cavity of freshly laid recipient embryos either previously compromised by gamma-radiation or not irradiated Injected eggs were incubated according to standard conditions. Cultured blastodermal cells were injected every week between 14 and 43 days of culture to determine the evolution of the potentialities of colonization with the culture time. All the embryos were analysed at 18 days of incubation.

The cultured blastodermal cells (donor cells) were from the colored Barred Rock or S86N strains, which are homozygous recessive (ii) at the dominant white locus I. Donor cells were injected into recipient embryos from the White Leghorn strain (recipient strain) which is homozygous dominant at the I locus. Somatic chimera could be identified at hatch by the presence of black down. Nevertheless, a PCR RFLP approach was developed to discriminate the genetic fingerprints from donor cells and recipient embryos (FIG. 6). The PCR RFLP pattern of the recipient strain is a 1 or 2 bands profile depending on the individual. The PCR RFLP pattern of the donor strain is a 3 bands profile. Chimeric tissues are identified by a 3 bands profile typical of the donor. It was then possible to determine whether the injected cells possessed the ability to colonize other tissues than the feathers. As was done for the expression of specific markers, the ability of in vitro colonization was studied while cells were maintained in long term culture and also according to the cell morphologies.

Several phenotypic (ie animals with feathers colonised by cells from the donor strain) and somatic chicken chimerae (ie animals with tissues other than the feathers colonised by cells from the donor strain) have been identified. The donor cells were shown to be present in the derivative of all three germ layers including the gonads. This results demonstrate that in vitro expanded chicken ES cells, obtained according to the method of the invention, could engraft and reconstitute various tissues of the recipient embryo including the gonads.

Surprisingly, the inventors demonstrate that injection of a larger amount of cells compared to amount recommended in the prior art (i.e around 300 to 500 irradiated cells), does not impact the viability of the embryos. Moreover, the percentage of phenotypic chimerism is significantly increased when large amount of cells (that is to say more than 15000 and eventually around 30000) are injected regardless of the presence or absence of the step of radiation. 30000 cells injected is not an upper limitation, and one considers injecting more cells, the only limitation being that the recipient embryo is able to survive and develop after having received these cells. The inventor demonstrate that injection of 15000 cells in irradiated recipient embryos and the injection of 30000 cells in non irradiated embryos give the best results, and specifically give the higher percentage of embryos chimeric in the gonads.

The inventors demonstrate that the used range of irradiation does not impact the viability of the chicken embryos. Moreover, the colonization potentiality did not seem to be dependent of the time length of blastodermal chicken cells in culture (data not shown).

Altogether the data support the notion that the in vitro isolated and amplified ES cells are true embryonic stem cells.

Example 3

Germ-Line Transmission by Chicken ES Cells

With the best methodologies of injection developed, 9% of the injected birds were chimeric in the gonads (data not shown). To address the issue of the germ-line transmission, a flock of 584 animals was generated by injection of cultured cells into recipient embryos according to the best methodologies shown to allow an optimal colonization of the gonads. The phenotypic chimerism of the birds extended from a few feathers at hatch, that were lost later on, to more than 95% at adulthood (FIG. 7 and table 2).

TABLE 2 extend of phenotypic chimerism of injected hens and roosters

| Hen identification | irradiation | N° of days in culture | % phenotypic chimerism | Potential N° of PGC injected |
|---|---|---|---|---|
| 2940 | X | 41 | 90 | 0.0025 |
| 1730 | X | 28 | 0 | 2.4 |
| 1692 | X | 21 | <5 | 0.064 |
| 4164 | no | 70 | <5 | <$10^{-3}$ |
| 4316 | no | 46 | at hatch only | <$10^{-3}$ |
| 4542 | X | 59 | 0 | $2.7 \times 10^{-8}$ |

Hens injected with Barred Rock cells were mated with Barred Rocks roosters to assess the contribution of the donor lineage to the germ-line. The germ-line transmission was assessed through examination of the distribution of black and yellow offspring. The progeny of 221 hens have been examined. Of 16006 F1 birds, 5 chicks exhibited variable percentage of white feathers (one was dead before hatch) and 1 chick presented plumage pigmentation typical from that of a Barred Rock (FIG. 8A). Description of the hens producing progeny with plumage pigmentation Barred-Rock-like and description of the conditions of injection are presented in the table 3. Even after 59 days of culture, cells remained able to colonize the germ-line. Germ-line transmission did not correlate with a high percentage of phenotypic chimerism of the hen. Indeed the mother of the Barred Rock-like chick was white. The potential number of PGC injected was estimated assuming that 50 PGC (Eyal-Giladi et al, 1976) are present in stage-X embryos. The final number of PGC was calculated according to the dilution factor resulting from the successive passages of the cells and the concentration and volume of cell suspension injected to the recipient embryo.

TABLE 3 influence of ES cells culture on in vivo colonization

| days in culture | % of phenotypic chimera | % of genotypic chimera |
|---|---|---|
| 14 | 2.3 | 0 |
| 22 | 6.4 | 0 |
| 29 | 11.1 | 0 |
| 37 | 11.6 | 0 |
| 43 | 6 | 1.3 (heart, liver, spleen, gonads) |

[% of phenotypic chimera: number of embryos with colored feathers/nb alive 18 days embryos; % of gentotypic chimera: nb of embryos chimeric in other tissues than the feathers/nb of alive 18 days embryos].

Four (4) out 5 chicks of F1 progeny (16006 birds) survived until adulthood. These 4 hens were inseminated with semen from Barred Rock roosters. The progeny of the hen 5664-5665 was Barred Rock like (FIG. 8B and table 4). Among the progeny of the other 3 hens were Barred Rocked-like and White Leghorn-like chicks (table 4).

TABLE 4

Progeny of F1 birds. Hens resulting from the mating of injected chimera with Barred Rock birds were inseminated with Barred Rock semen. Eggs were incubated until hatch. The phenotype of the progeny was recorded.

| Hen Identification | N° progeny | Progeny phenotype |
|---|---|---|
| 5664-5665 (Barred Rock) | 6 | Barred Rock |
| 5660-5661 | 13 | 5 Barred Rock 8 White Leghorn |
| 5650-5651 | 8 | 3 Barred Rock 5 White Leghorn |
| 5662-5663 | 13 | 7 Barred Rock 6 White Leghorn |

The inventors provide a method of culture chicken ES cells. Amplification of blastodermal cells had been documented only for White Leghorn and Barred Rock chicken strains (Pain et al, 1996 Dev. 122(8) 2339-2348), Petitte et al 1990 108(1):185-189, Zhu et al, 2005 Nat. Biotechnol. 23(9): 1159-1169). The culture process developed in this study, in particular the combination of specific growth factors and its evolution during time allowed reproducibly isolating and amplifying cells from different chicken strains. The efficacy of amplification was strain dependant, a result consistent with the strain difference in establishment of ES cells lines described for the mouse (Kawase et al, 1994 Int. J. Dev. Biol. 38(2):385-390). Interestingly and unlike mouse, totipotency of chick ES cells maintained in long term culture is supported by a deprivation of several growth factors. That is to say that chicken ES cells do preserve totipotency during long term culture in complete culture medium, and also in complete medium deprived with growth factors such as IL-6, IL-6R, SCF and FGF. Of note, human ES cells cannot be either maintained in the culture conditions established for mouse ES cells.

Pain et al (1996) described, in chicken blastodermal long-term cultures (more than 160 days), large colonies of small cells, tightly packed in nests with typical "ES-like" morphological features similar to that of mouse ES cells. By contrast, the morphology of chicken blastodermal cells that the inventor maintained in long-term culture did not remain so stable and changed from cells with a round shape that were tightly connected to cells with looser connections. This morphological evolution was consistent and independent of the chicken strain. This change in morphology did not affect the self-renewal property specific of ES cells. The potential commitment of the cells in different lineages was addressed by (i) the biochemical characterization of the cells by immunofluorescence or RT PCR analysis; (ii) a transgenesis methodology to access to the biological property of the cultured cells. Cells have been characterized with respect to markers specific of all three germ layers, ectoderm, mesoderm and endoderm. Markers indicative of a very early differentiation were selected. None of the morphologies did present a specific combination of markers. Markers of undifferentiated cells, markers of all three germ layers could be detected as well as a marker of the germ-line like vasa. There was no evolution of markers expression specific of a change of morphology. Even cells with the most differentiated morphology expressed markers specific of ES cells and did not express markers of differentiation.

In vitro amplified cells suspensions were injected into recipient embryos. The feather pigmentation results from a transfer of pigments from the melanocytes to the shaft of the feathers. Melanocytes derived from neural crest cells of the trunk of the embryo. The differentiation of neural crest cells happens very early in the development of an embryo. Pigmentation of the plumage of white recipient embryos injected with cells from a black strain of chicken might not reflect the totipotency of the injected cells but might indicate that cells committed to the melanocyte lineage were able to join the melanoblastic lineage of the recipient. Thus the study of the contribution of the injected cells to the recipient embryo was not restricted to the observation of the plumage but included tissues derivatives of all three germ layers. Phenotypic and somatic chimera were obtained with each of the main morphologies of cells observed in culture (cords, clumps and comets) supporting the undifferentiated status of the cells regardless of the morphology. Interestingly the gonads were also colonized by the injected cells.

The ultimate proof of the ES status of a cell is the germ-line transmission. 1 F0 (injected) hen (0.3%) supported germ-line transmission, Over the 16 chicks progeny of this hen, 1 F1 chick was Barred Rock-like (6.25%). All the F2 chicks from the F1 hen presented the Barred Rock phenotype which indicates that the acquisition of the donor traits is stable through several generations. Half of the progeny of the F1 hens that presented variable percentage of black feathers was Barred Rock-like and the other half had a White Leghorn phenotype as expected from Mendel inheritance rules.

Thus the inventors demonstrate the germ-line competence of chicken blastodermal cells. Chicken blastodermal cells are thus useful to develop avian transgenesis.

Example 4

Isolation and Amplification of Duck ES Cells 4.1—Raw Material
Duck Eggs

Duck eggs from Pekin strains GL30 were obtained from GRIMAUD FRERES SELECTION (La Corbière, Roussay France). The parent ducks were vaccinated against *Escherichia Coli* (Autogenous vaccine *Coli* 01 & 02), *Pasteurella multocida* (Landavax), Duck viral hepatitis (Hepatovax), *Erysipelothrix rhusiopathiae* (Ruvax), Avian metapneumovirus (Nemovac), *Salmonella typhimurium* & Enteridis (Autogenous vaccine), *Riemerella antipestifer* (Autovaccine *Riemerella*), Avian metapneumovirus (Nobilis RTV inactive) and *Erysipelothrix rhusiopathiae* (Ruvax). After receipt, fertilized Pekin duck eggs were submitted to a disinfection in an hypochloryde bath followed by a decontamination with Fermacidal (Thermo) to avoid any risk of contamination linked to dusts attached on the shell.

Feeder Cells

Cells from murine origin (STO cells) were used as feeder layer to maintain the pluripotency of duck stem cells. Those feeder cells are mitotically inactivated by gamma irradiation (45 to 55 Grays) before seeding on plastic. This dose of irradiation is a sub-lethal dose that induces a definitive arrest of the cell cycle but still permits the production of growth factors and extracellular matrix, necessary for the promotion of the cell growth of non differentiated cells. The STO cell line was derived by A. Bernstein, Ontario Cancer Institute, Toronto, Canada from a continuous line of SIM (Sandos Inbred Mice) mouse embryonic fibroblasts and it was supplied by the American Type Culture Collection (ATCC) (STO Product number: CRL-1503, Batch number 1198713). Fresh feeder layers were prepared twice a week. Exponentially cells were dissociated and counted. A part of cells were seeded for maintenance of viable cultures and another part was irradiated. For irradiation, we prepared a cell suspension at $10 \times 10^6$ cells/mL in tubes. Cells were exposed to a 45 to 55 grey dose and were seeded on plastic. After seeding, dishes or plates coated with inactivated feeder cells were used during a maximum of 5 days.

Medium
Medium GTM-3 (Sigma, Cat n° G9916)
DMEM-HamF12 (Cambrex, Cat n° BE04-687)
Additives
Glutamine (Cambrex, Cat n° BE17-605E)
Antibiotics: Pencillin/streptomycin (Cambrex, Cat n° BE17-602E))
Non essential Amino Acids (Cambrex, Cat n° BE13-114E)
Sodium pyruvate (Cambrex, Cat n° BE13-115)
Vitamins (Cambrex, Cat n° 13-607C)
Beta Mercapto Ethanol (Sigma, Cat n° M7522)
Yeastolate (SAFC, Cat n° 58902C)
Factors
  Six different recombinant factors were used:
  Recombinant Human Ciliary Neurotrophic Factor (CNTF) (Peprotech Inc, Cat n° 450-13)
  Recombinant Human Insulin Like Factor I (IGF1) (Peprotech Inc, Cat n° 100-11)
  Recombinant Human Interleukin 6 (IL6) (Peprotech Inc, Cat n° 200-06)
  Recombinant Human soluble Interleukin 6 receptor (sIL6r) (Peprotech Inc, Cat n° 200-06 R)
  Recombinant Human Stem Cell Factor (SCF) (Peprotech Inc, Cat n° 300-07)
  Recombinant Human basic Fibroblast Growth Factor (bFGF) (Peprotech Inc, Cat n° 100-18B)
  All those factors, excepted IL6r, are produced in *E. Coli* bacteria. Soluble IL6r is expressed in transfected HEK293 cells.

Fetal Bovine Serum
Non Irradiated Fetal Bovin Serum (FBS) (JRH, Cat n° 12003)
The non irradiated serum used in the program was collected and produced in Australia. Animals used for collection were USDA inspected and acceptable for slaughter. It was added in the medium during avian stem cells culture. This batch was not submitted to irradiation to avoid the destruction of critical proteins or components that may be essential for the maintenance of stem cells in culture.

Irradiated Serum (JRH, Cat n° 12107)

The irradiated batch used in this program was collected in United States. This irradiated batch was added as supplement in the DMEM medium used for the culture of STO cells (feeder cells). Those cells do not require as stem cells a specific quality of serum for growth and maintenance in culture. To minimize high concentration of serum in the medium we have adapted the STO cells to grow in presence of 4% of FBS only.

4.2—Process of Isolation and Culture of Duck ES Cells

Around 360 Fertilized duck eggs were opened, the yolk were separated from the albumen during the opening. The embryos were removed from the yolk with the aid of a small absorbent filter paper (Whatmann 3M paper), cut out beforehand in the form of a perforated ring with the aid of a punch. The diameter of the perforation is about 5 mm. These small rings were sterilized using dry heat for about 30 minutes in an oven. In practice, during the step of embryo collection, a small paper ring is deposited on the surface of the yolk and centered on the embryo which is thus surrounded by the paper ring. The latter is then cut out with the aid of small pairs of scissors and the whole removed is placed in a Petri dish, filled with PBS. The embryos thus carried away by the ring were cleaned of the excess yolk in the medium and the embryonic disk, thus free of the excess vitellin, were collected with a Pasteur pipette.

The duck embryos were placed in 50 mL tubes containing PBS 1× The duck embryos were then mechanically dissociated, washed with PBS, and seeded on an inactivated layer of feeder STO cells into complete culture medium at 39° C., 7.5% $CO_2$. The feeder cells were seeded in 6 well plates or dishes at around $2.7 \times 10^4$ cell/cm$^2$. The complete culture medium is composed of serum free medium DMEM-Ham F12 supplemented with 10% fetal bovine serum, with IGF1, CNTF, and optionally Il-6, Il-6R, SCF and Bovine FGF, at a final concentration of 1 ng/ml, and with 1% non-essential amino acids, with 1% of mixture of vitamins of commercial origin, with sodium pyruvate at a final concentration of 0.1 mM, with beta-mercapto-ethanol at a final concentration of 0.5 mM, glutamine at a final concentration of 2.1 mM, penicillin at a final concentration of 100 U/ml, streptomycin at a final concentration of 100 µg/ml and yeastolate 1×. Rapidly at the passage 4, the mixture of antibiotics is no longer added to the medium.

The duck ES cells were cultured in the DMEM-Ham F12 complete culture medium up to passage 4. After passage 4, the base medium is modified and DMEM-Ham F12 complete medium is replaced either by:

the GTM-3 medium supplemented with 10% fetal bovine serum and with IGF1 and CNTF at a final concentration of 1 ng/ml, with 1% non-essential amino acids, with 1% of mixture of vitamins of commercial origin, with sodium pyruvate at a final concentration of 0.1 mM, with beta-mercapto-ethanol at a final concentration of 0.5 mM, glutamine at a final concentration of 2.1 mM and yeastolate 1×; or the GTM-3 medium supplemented with 10% fetal bovine serum and with IGF1, CNTF, Il-6, Il-6R, SCF, FGF at a final concentration of 1 ng/ml, with 1% non-essential amino acids, with 1% of mixture of vitamins of commercial origin, with sodium pyruvate at a final concentration of 0.1 mM, with beta-mercapto-ethanol at a final concentration of 0.5 mM, glutamine at a final concentration of 2.1 mM and yeastolate 1×.

The duck ES cells were further cultured during at least 14 passages in this new medium of culture without differentiation.

The invention claimed is:

1. A method of obtaining chicken embryonic stem (ES) cells comprising the steps of:
   a) isolating and dissociating the blastoderm disk of fertilized un-incubated chicken embryos between development stages VI and XII;
   b) culturing the cells obtained in step a) in a basal culture medium supplemented with IGF-1, CNTF, IL-6, IL-6R, SCF, and bFGF with a layer of feeder cells and animal serum; and
   c) culturing the cells obtained in step b) in basal culture medium supplemented with IGF-1 and CNTF as the only supplemental growth factors with a layer of feeder cells and animal serum such that chicken ES cells are obtained.

2. The method according to claim 1 wherein the ES cells obtained in step d) are maintained in said culture medium for at least 14 days.

3. The method according to claim 1 wherein said feeder cells are mouse fibroblast cells.

4. The method according to claim 1 wherein the concentration of the growth factors IGF-1 and CNTF is about 1 ng/ml.

5. The method according to claim 1 wherein the ES cells obtained in step d) are maintained in said culture medium at 39° C. in 7.5% CO2.

6. The method according to claim 1 wherein said basal culture medium is selected from the group consisting of BME (basal Eagle Medium), MEM (minimum Eagle Medium), medium 199, DMEM (Dulbecco's modified Eagle Medium), GMEM (Glasgow modified Eagle medium), DMEM-HamF12, Ham-F12 and Ham-F10, Iscove's Modified Dulbecco's medium, MacCoy's 5A medium, RPMI 1640 and GTM-3 medium.

7. The method according to claim 1 wherein said basal culture medium is DMEM-HamF12.

8. The method according to claim 7 wherein said DMEM-HamF12 is complemented with 0.16 mM betamercaptoethanol, 1% non-essential amino acids, 1 mM sodium pyruvate, and 2 mM L-Glutamine.

9. The method according to claim 1 wherein said basal culture medium is DMEM-HamF12 supplemented with 10% fetal calf serum, 0.16 mM betamercaptoethanol, 1% non-essential amino acids, 1 mM sodium pyruvate, 2 mM L-Glutamine, 1 ng/ml IGF-1, 1 ng/ml CNTF and 1% penis-treptomycine.

10. The method according to claim 1 wherein said chicken embryos are fertilized un-incubated chicken embryos at development stage X.

11. The method according to claim 1, wherein in step b) cells are cultured for at least between 2 to 10 passages.

* * * * *

SEQUENCE LISTING

```
<160> NUMBER OF SEQ ID NOS: 14

<210> SEQ ID NO 1
<211> LENGTH: 21
<212> TYPE: DNA
<213> ORGANISM: Artificial sequence
<220> FEATURE:
<223> OTHER INFORMATION: Forward primer

<400> SEQUENCE: 1
ggtgtaaata tcaaaattat c                                              21

<210> SEQ ID NO 2
<211> LENGTH: 21
<212> TYPE: DNA
<213> ORGANISM: Artificial sequence
<220> FEATURE:
<223> OTHER INFORMATION: Reverse primer

<400> SEQUENCE: 2
cggttaaaat acgaatagag a                                              21

<210> SEQ ID NO 3
<211> LENGTH: 21
<212> TYPE: DNA
<213> ORGANISM: Artificial sequence
<220> FEATURE:
<223> OTHER INFORMATION: Forward primer

<400> SEQUENCE: 3
```
ctatgagcag ttacgagggt c                                          21

<210> SEQ ID NO 4
<211> LENGTH: 20
<212> TYPE: DNA
<213> ORGANISM: Artificial sequence
<220> FEATURE:
<223> OTHER INFORMATION: Reverse primer

<400> SEQUENCE: 4
cggaccaaca ggctagtctc                                            20

<210> SEQ ID NO 5
<211> LENGTH: 23
<212> TYPE: DNA
<213> ORGANISM: Artificial sequence
<220> FEATURE:
<223> OTHER INFORMATION: Vasa forward primer

<400> SEQUENCE: 5
tttggtacta gatgaagcag acc                                        23

<210> SEQ ID NO 6
<211> LENGTH: 21
<212> TYPE: DNA
<213> ORGANISM: Artificial sequence
<220> FEATURE:
<223> OTHER INFORMATION: Vasa reverse primer

<400> SEQUENCE: 6
gttccctatc tccatgaatg c                                          21

<210> SEQ ID NO 7
<211> LENGTH: 22
<212> TYPE: DNA
<213> ORGANISM: Artificial sequence
<220> FEATURE:
<223> OTHER INFORMATION: Brachyury forward primer

<400> SEQUENCE: 7
cacaaagaca tgatggagga ag                                         22

<210> SEQ ID NO 8
<211> LENGTH: 22
<212> TYPE: DNA
<213> ORGANISM: Artificial sequence
<220> FEATURE:
<223> OTHER INFORMATION: Brachyury forward primer 2

<400> SEQUENCE: 8
tgaagtcctc tccaaaacca tt                                         22

<210> SEQ ID NO 9
<211> LENGTH: 22
<212> TYPE: DNA
<213> ORGANISM: Artificial sequence
<220> FEATURE:
<223> OTHER INFORMATION: Brachyury reverse primer

<400> SEQUENCE: 9
cataagttcg ggtactgact gg                                         22

<210> SEQ ID NO 10
<211> LENGTH: 22
<212> TYPE: DNA
<213> ORGANISM: Artificial sequence

```
<220> FEATURE:
<223> OTHER INFORMATION: Brachyury reverse primer 2

<400> SEQUENCE: 10
cacaaaatca ttctgcggta aa                                              22

<210> SEQ ID NO 11
<211> LENGTH: 24
<212> TYPE: DNA
<213> ORGANISM: Artificial sequence
<220> FEATURE:
<223> OTHER INFORMATION: GAPDH forward primer

<400> SEQUENCE: 11
aggtgctgag tatgttgtgg agtc                                            24

<210> SEQ ID NO 12
<211> LENGTH: 21
<212> TYPE: DNA
<213> ORGANISM: Artificial sequence
<220> FEATURE:
<223> OTHER INFORMATION: GAPDH reverse primer

<400> SEQUENCE: 12
agaactgagc ggtggtgaag a                                               21

<210> SEQ ID NO 13
<211> LENGTH: 22
<212> TYPE: DNA
<213> ORGANISM: Artificial sequence
<220> FEATURE:
<223> OTHER INFORMATION: Thy-1 forward primer

<400> SEQUENCE: 13
aggacaacag gaagcacatc at                                              22

<210> SEQ ID NO 14
<211> LENGTH: 22
<212> TYPE: DNA
<213> ORGANISM: Artificial sequence
<220> FEATURE:
<223> OTHER INFORMATION: Thy-1 reverse primer

<400> SEQUENCE: 14
gttctggatc aagaggctga ag                                              22
```